(12) United States Patent
Gutsche et al.

(10) Patent No.: US 8,709,513 B2
(45) Date of Patent: Apr. 29, 2014

(54) LIQUID FORMULATIONS OF CARBOXAMIDE ARTHROPODICIDES

(75) Inventors: Oliver Walter Gutsche, Wilmington, DE (US); Isaac Billy Annan, Newark, DE (US); Hector Eduardo Portillo, Bear, DE (US)

(73) Assignee: E I du Pont de Nemours and Company, Wilmington (DE)

( * ) Notice: Subject to any disclaimer, the term of this patent is extended or adjusted under 35 U.S.C. 154(b) by 450 days.

(21) Appl. No.: 12/514,553

(22) PCT Filed: Nov. 30, 2007

(86) PCT No.: PCT/US2007/024676
§ 371 (c)(1),
(2), (4) Date: May 12, 2009

(87) PCT Pub. No.: WO2008/069990
PCT Pub. Date: Jun. 12, 2008

(65) Prior Publication Data
US 2010/0055084 A1    Mar. 4, 2010

Related U.S. Application Data

(60) Provisional application No. 60/872,095, filed on Dec. 1, 2006, provisional application No. 60/995,846, filed on Sep. 28, 2007.

(51) Int. Cl.
| | | |
|---|---|---|
| *A61K 36/48* | (2006.01) | |
| *A61K 31/16* | (2006.01) | |
| *A01N 63/00* | (2006.01) | |
| *C07D 401/00* | (2006.01) | |
| *A61K 31/44* | (2006.01) | |
| *A61K 36/00* | (2006.01) | |

(52) U.S. Cl.
USPC ............... 424/757; 424/93.6; 424/93.461; 424/776; 514/341; 514/616; 546/275.4

(58) Field of Classification Search
None
See application file for complete search history.

(56) References Cited

U.S. PATENT DOCUMENTS

| | | | |
|---|---|---|---|
| 6,479,432 B1 | 11/2002 | Sixl | |
| 6,603,044 B1 | 8/2003 | Tohnishi et al. | |
| 6,747,047 B2 | 6/2004 | Lahm et al. | |
| 7,232,836 B2 | 6/2007 | Lahm et al. | |
| 7,247,647 B2 | 7/2007 | Hughes et al. | |
| 2004/0198984 A1* | 10/2004 | Lahm et al. | 546/275.4 |
| 2004/0209923 A1 | 10/2004 | Berger et al. | |
| 2006/0014808 A1* | 1/2006 | Hughes et al. | 514/359 |
| 2007/0281860 A1 | 12/2007 | Baur et al. | |
| 2008/0027046 A1 | 1/2008 | Annan et al. | |
| 2008/0221167 A1 | 9/2008 | Fischer et al. | |
| 2008/0275061 A1 | 11/2008 | Lahm et al. | |
| 2008/0305093 A1 | 12/2008 | Gutsche et al. | |
| 2009/0104145 A1 | 4/2009 | Annan et al. | |

FOREIGN PATENT DOCUMENTS

| | | |
|---|---|---|
| AU | 88259/91 | 6/1992 |
| DE | 37 82 937 T2 | 5/1993 |
| EP | 0299961 B1 | 12/1992 |
| RU | 2142229 C | 12/1999 |
| WO | 01/30156 A1 | 5/2001 |
| WO | WO03/015519 | 2/2003 |
| WO | 03/028465 A1 | 4/2003 |
| WO | WO2004/067528 | 8/2004 |
| WO | WO2005/084435 | 9/2005 |
| WO | WO2006/008108 | 1/2006 |
| WO | WO2006/111341 | 10/2006 |
| WO | WO2007/081553 | 7/2007 |
| WO | WO2009/002810 | 12/2008 |
| WO | WO2009/002856 | 12/2008 |

OTHER PUBLICATIONS

Office Actions mailed Jun. 23, 2010; Dec. 6, 2010; and Jun. 30, 2011, in co-pending U.S. Appl. No. 11/628,145.
Office Action mailed Sep. 21, 2011, in co-pending U.S. Appl. No. 12/159,124.
Grounds of Opposition to EP2094092B1 dated Jul. 29, 2013.
Knowles, A., New Developments in Crop Protection Product Formulation, Agrow Reports DS243, T&F Informa UK Ltd, May 2005, p. 58 und 188.
Reekmans, S., Novel surfactant and adjuvants for agrochemicals, in: Chemistry and Technology of Agrochemical Formulations, Ed. A Knowles, Kluwer Academic Publishers, 1998, Chapter 7.1., p. 179-195.
Knowles, A., Improving agrochemical Formulations, Ed. A Knowles, Kluwer Academic Publishers, 1998, Chapter 8.2.2, p. 237-239.
Anonym, Surfactant and oil-based adjuvants in agricultural applications, Ed.: Frost & Sullivan, 2001, p. 139.

* cited by examiner

*Primary Examiner* — Chris R Tate
*Assistant Examiner* — Russell Fiebig

(57) ABSTRACT

Disclosed are suspension concentrate compositions comprising by weight based on the total weight of the composition, (a) from about 0.1 to about 50% of one or more carboxamide arthropodicides that are solid at room temperature; (b) from 0 to about 50% of one or more biologically active agents other than the carboxamide arthropodicides; (c) from about 20 to about 70% of water; (d) from about 10 to about 70% of one or more water-immiscible liquid compounds; and (e) from about 1 to about 55% of a surfactant component having a dispersing property. This invention also relates to a method for controlling an arthropod pest comprising diluting said suspension concentrate composition with water, optionally adding an adjuvant to form a diluted composition, and contacting the arthropod pest or its environment with an effective amount of said diluted composition.

14 Claims, No Drawings

LIQUID FORMULATIONS OF CARBOXAMIDE ARTHROPODICIDES

This application is a 371 national stage entry of PCT/US07/24676, internationally filed on Nov. 30, 2007. PCT/US07/24676 claims priority from Provisional Application No. 60/872,095, filed on Dec. 1, 2006 and from Provisional Application No. 60/995,846, filed on Sep. 28, 2007.

FIELD OF THE INVENTION

This invention relates to certain aqueous suspension concentrate arthropodicidal compositions comprising at least one solid carboxamide arthropodicide and a water-immiscible liquid compound, a method for producing the compositions, and the use of the compositions of the invention for controlling arthropods.

BACKGROUND OF THE INVENTION

Anthranilamides (see U.S. Pat. No. 6,747,047, PCT Publications WO 2003/015519 and WO 2004/067528) and phthalic diamides (see U.S. Pat. No. 6,603,044) are recently discovered classes of carboxamide arthropodicides having activity against numerous arthropod pests of economic importance.

Carboxamide arthropodicides like other agricultural chemicals can be formulated as concentrates in a variety of different forms, including liquid compositions such as suspension concentrates and solid compositions such as wettable powders and granules.

Typically chemical compounds for protecting plants, e.g., arthropodicides, are formulated as compositions (formulations) comprising the active compound(s) and inert ingredients such as carriers and adjuvants. These compositions can be applied by the user to the target plants/pests undiluted or after dilution with water. Liquid formulation concentrates are among the most commonly used formulations for plant protection chemicals, because they can be easily measured and poured, and when diluted with water typically form easily sprayed aqueous solutions or dispersions.

Because the efficacy and chemical stability of the active ingredient and physical stability of the formulated composition may be affected by inert ingredients in the formulation, suitable inert ingredients should not cause decomposition of the active ingredient, substantially diminish its activity on application, or cause appreciable precipitation or crystal formation upon long-term storage. Furthermore, inert ingredients should be nonphytotoxic and environmentally safe. Inert ingredients of formulations intended for dilution with water before application should be easily dissolved or dispersed in water. In certain formulations inert ingredients (often termed adjuvants) can even enhance the biological performance of the active ingredient by facilitating penetration or uptake into the plant or arthropod pest or by increasing resistance to wash-off. While such adjuvant properties are not essential, they are highly desirable.

Water is a particularly desirable formulating ingredient, because it is very inexpensive, environmentally safe and compatible with further dilution with water before spraying. Although aqueous suspension concentrates comprising active ingredient together with typical aqueous suspension formulating ingredients are useful formulations for carboxamide arthropodicides, improved properties such as increased resistance to settling, greater arthropodicidal efficacy and greater resistance to wash-off are always desirable. Aqueous suspension concentrate formulations of carboxamide arthropodicides having improved properties have now been discovered.

SUMMARY OF THE INVENTION

This invention is directed to an arthropodicidal suspension concentrate composition comprising by weight based on the total weight of the composition:
 (a) from about 0.1 to about 50% of one or more carboxamide arthropodicides that are solid at room temperature;
 (b) from 0 to about 50% of one or more biologically active agents other than the carboxamide arthropodicides;
 (c) from about 20 to about 70% of water;
 (d) from about 10 to about 70% of one or more water-immiscible liquid compounds; and
 (e) from about 1 to about 55% of a surfactant component having a dispersing property.

This invention also relates to a method for controlling an arthropod pest comprising diluting said suspension concentrate composition with water and optionally adding an adjuvant to form a diluted composition, and contacting the arthropod pest or its environment with an effective amount of said diluted composition.

DETAILS OF THE INVENTION

As used herein, the terms "comprises," "comprising," "includes," "including," "has," "having" or any other variation thereof, are intended to cover a non-exclusive inclusion. For example, a composition, process, method, article, or apparatus that comprises a list of elements is not necessarily limited to only those elements but may include other elements not expressly listed or inherent to such composition, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular. The phrases "at least one" and "one or more" have the same meaning.

The term "suspension concentrate composition" and derivative terms such as "an arthropodicidal suspension concentrate composition" refer to compositions comprising finely divided solid particles of an active ingredient dispersed in a continuous liquid phase. Said particles retain identity and can be physically separated from the continuous liquid phase.

Although alkoxylated fatty acid esters can be regarded as non-ionic surfactants, these esters can also be used as water-immiscible liquid compounds having self-emulsifying ability. Therefore in the present disclosure and claims, if component (d) in the present composition comprises one or more water-immiscible liquid compounds other than alkoxylated fatty acid esters, wherein the total amount by weight of said one or more water-immiscible liquid compounds is greater than the total amount of alkoxylated fatty acid esters present in the composition, then any alkoxylated fatty acid esters are considered to relate to component (e) (i.e. the surfactant component having a dispersing property) and not component (d).

Otherwise, the one or more alkoxylated fatty acid esters in the composition are considered to relate to component (d). For example, if the composition contains 40% methylated soybean oil and 20% ethoxylated soybean oil by weight of composition, then the ethoxylated soybean oil is considered to relate to component (e). If the composition contains 30% methylated soybean oil and 40% ethoxylated soybean oil, then the ethoxylated soybean oil is considered to relate to component (d).

Depending upon molecular structure, a particular surfactant may have more than one useful surfactant property. For example, a surfactant may be useful both as a dispersant and wetting agent. As another example, a surfactant may be useful as a dispersant, an emulsifier and a wetting agent. The surfactant properties of commercially available surfactants are published in technical bulletins and compendia. In the present disclosure and claims, description of a surfactant as having a particular surfactant property does not necessarily indicate that the surfactant lacks other useful surfactant properties.

As disclosed herein for embodiments of the present invention, percentage amounts of surfactants having a dispersing property (i.e. dispersants), percentage amounts of surfactants having an emulsifying property (i.e. emulsifiers), percentage amounts of surfactants having a wetting property (i.e. wetting agents) and percentage amounts of surfactants having a defoaming property (i.e. defoamers or anti-foaming agents) may be specified in ranges or as upper or lower limits for the composition. For percentage amount calculations the pertinent classification of a surfactant having more than one useful surfactant property is determined according to the following ranking methodology. If a surfactant is useful as a dispersant, it is classified as a surfactant having a dispersing property for the purpose of calculating percentage amounts of surfactants having particular properties in the composition. If a surfactant is useful as an emulsifier, but not a dispersant, it is classified as a surfactant having an emulsifying property for the purpose of calculating percentage amounts of surfactants having particular properties. If a surfactant is useful as a wetting agent, but not a dispersant or emulsifier, it is classified as a surfactant having a wetting property for the purpose of calculating percentage amounts of surfactants having particular properties. If a surfactant is useful as a defoamer, but not a dispersant, emulsifier or wetting agent, it is classified as a surfactant having a defoaming property for the purpose of calculating percentage amounts of surfactants having particular properties. For example, if a surfactant has dispersing, emulsifying and wetting properties, for purpose of percentage amount calculations, it contributes to just the percentage amounts calculated for surfactants having dispersing properties (which has the highest ranking) but not to the percentage amounts calculated for surfactants having emulsifying or dispersing properties in the composition. This ranking methodology relates only to determining how to classify a surfactant for the purpose of calculating percentage amounts of surfactants having particular properties. Although a surfactant having dispersing, emulsifying and wetting properties is counted only as a dispersant for the purpose of calculating percentage amounts, such a surfactant is otherwise considered to be a surfactant having a dispersing property, a surfactant having an emulsifying property, and a surfactant having an wetting property, and to provide these properties to component (e) of the composition.

Embodiment Note 1. Of note is an arthropodicidal suspension concentrate composition comprising by weight based on the total weight of the composition:
(a) from about 0.1 to about 50% of one or more carboxamide arthropodicides that are solid at room temperature;
(b) from 0 to about 50% of one or more biologically active agents other than the carboxamide arthropodicides;
(c) from about 20 to about 70% of water;
(d) from about 10 to about 60% of one or more water-immiscible liquid compounds;
(e1) from about 1 to about 15% of one or more dispersing agents; and
(e2) from about 0 to about 20% of one or more emulsifiers.

Further embodiments of the present invention include:

Embodiment 1. The composition described in the Summary of the Invention or Embodiment Note 1 wherein component (a) (i.e. the one or more carboxamide arthropodicides that are solid at room temperature) comprises a carboxamide arthropodicide having a melting point above about 80° C.

Embodiment 1A. The composition of Embodiment 1 wherein component (a) comprises a carboxamide arthropodicide having a melting point above about 100° C.

Embodiment 1B. The composition of Embodiment 1A wherein component (a) comprises a carboxamide arthropodicide having a melting point above about 120° C.

Embodiment 2. The composition described in the Summary of the Invention or Embodiment Note 1 wherein component (a) (i.e. the one or more carboxamide arthropodicides that are solid at room temperature) is selected from anthranilamides of Formula 1, N-oxides, and salts thereof,

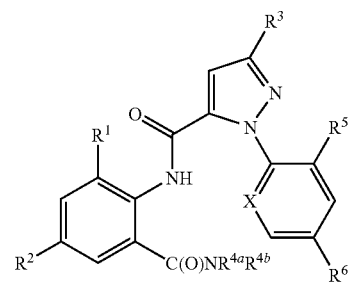

wherein
X is N, CF, CCl, CBr or CI;
$R^1$ is $CH_3$, Cl, Br or F;
$R^2$ is H, F, Cl, Br or cyano;
$R^3$ is F, Cl, Br, $C_1$-$C_4$ haloalkyl or $C_1$-$C_4$ haloalkoxy;
$R^{4a}$ is H, $C_1$-$C_4$ alkyl, cyclopropylmethyl or 1-cyclopropylethyl;
$R^{4b}$ is H or $CH_3$;
$R^5$ is H, F, Cl or Br; and
$R^6$ is H, F, Cl or Br.

Embodiment 2A. The composition of Embodiment 2 wherein component (a) is selected from anthranilamides of Formula 1, N-oxides, and salts thereof, wherein X is N; $R^1$ is $CH_3$; $R^2$ is Cl or cyano; $R^3$ is Cl, Br or $CF_3$; $R^{4a}$ is $C_1$-$C_4$ alkyl; $R^{4b}$ is H; $R^5$ is Cl; and $R^6$ is H.

Embodiment 2B. The composition of Embodiment 2 wherein component (a) is selected from anthranilamides of Formula 1, N-oxides, and salts thereof, wherein X is N; $R^1$ is $CH_3$; $R^2$ is Cl or cyano; $R^3$ is Cl, Br or $CF_3$; $R^{4a}$ is Me or $CH(CH_3)_2$; $R^{4b}$ is H; $R^5$ is Cl; and $R^6$ is H.

Embodiment 2C. The composition of Embodiment 2 wherein component (a) is selected from the group consisting of:

N-[4-chloro-2-methyl-6-[[(1-methylethyl)amino]carbonyl]phenyl]-1-(3-chloro-2-pyridinyl)-3-(trifluoromethyl)-1H-pyrazole-5-carboxamide, N-[4-chloro-2-methyl-6-[(methylamino)carbonyl]phenyl]-1-(3-chloro-2-pyridinyl)-3-(trifluoromethyl)-1H-pyrazole-5-carboxamide, 3-bromo-N-[4-chloro-2-methyl-6-[[(1-methylethyl)amino]carbonyl]phenyl]-1-(3-chloro-2-pyridinyl)-1H-pyrazole-5-carboxamide, 3-bromo-N-[4-chloro-2-methyl-6-[(methylamino)carbonyl]phenyl]-1-(3-chloro-2-pyridinyl)-1H-pyrazole-5-carboxamide, 3-bromo-1-(3-chloro-2-pyridinyl)-N-[4-cyano-2-methyl-6-[(methylamino)-carbonyl]phenyl]-1H-pyrazole-5-carboxamide, 1-(3-chloro-2-pyridinyl)-N-[4-cyano-2-methyl-6-[(methylamino)carbonyl]-phenyl]-3-(trifluoromethyl)-1H-pyrazole-5-carboxamide, 3-bromo-1-(2-chlorophenyl)-N-[4-cyano-2-methyl-6-[[(1-methylethyl)-amino]carbonyl]phenyl]-1H-pyrazole-5-carboxamide, 3-bromo-1-(2-chlorophenyl)-N-[4-cyano-2-methyl-6-[(methylamino)-carbonyl]phenyl]-1H-pyrazole-5-carboxamide, 3-bromo-1-(2-chlorophenyl)-N-[2,4-dichloro-6-[(methylamino)carbonyl]-phenyl]-1H-pyrazole-5-carboxamide, 3-bromo-N-[4-chloro-2-[[(cyclopropylmethyl)amino]carbonyl]-6-methyl-phenyl]-1-(3-chloro-2-pyridinyl)-1H-pyrazole-5-carboxamide, 3-bromo-1-(3-chloro-2-pyridinyl)-N-[4-cyano-2-[[(cyclopropylmethyl)-amino]-carbonyl]-6-methylphenyl]-1H-pyrazole-5-carboxamide, 3-bromo-N-[4-chloro-2-[[(1-cyclopropylethyl)amino]carbonyl]-6-methyl-phenyl]-1-(3-chloro-2-pyridinyl)-1H-pyrazole-5-carboxamide, and 3-bromo-1-(3-chloro-2-pyridinyl)-N-[4-cyano-2-[[(1-cyclopropylethyl)-amino]carbonyl]-6-methylphenyl]-1H-pyrazole-5-carboxamide.

Embodiment 3. The composition described in the Summary of the Invention or Embodiment Note 1 wherein component (a) (i.e. the one or more carboxamide arthropodicides that are solid at room temperature) is selected from phthalic diamides of Formula 2 and salts thereof,

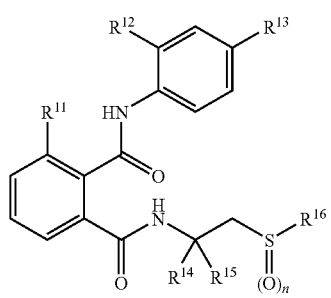

2 wherein
$R^{11}$ is $CH_3$, Cl, Br or I;
$R^{12}$ is $CH_3$ or Cl;
$R^{13}$ is $C_1$-$C_3$ fluoroalkyl;
$R^{14}$ is H or $CH_3$;
$R^{15}$ is H or $CH_3$;
$R^{16}$ is $C_1$-$C_2$ alkyl; and
n is 0, 1 or 2.

Embodiment 3A. The composition of Embodiment 3 wherein component (a) is selected from phthalic diamides of Formula 2 and salts thereof, wherein $R^{11}$ is Cl, Br or I; $R^{12}$ is $CH_3$; $R^{13}$ is $CF_3$, $CF_2CF_3$ or $CF(CF_3)_2$; $R^{14}$ is H or $CH_3$; $R^{15}$ is H or $CH_3$; $R^{16}$ is $CH_3$; and n is 0, 1 or 2.

Embodiment 3B. The composition of Embodiment 3 wherein component (a) is $N^2$-[1,1-dimethyl-2-(methylsulfonyl)ethyl]-3-iodo-$N^1$-[2-methyl-4-[1,2,2,2-tetrafluoro-1-(trifluoromethyl)ethyl]phenyl]-1,2-benzenedicarboxamide.

Embodiment 4. The composition described in the Summary of the Invention or Embodiment Note 1 wherein component (a) (i.e. the one or more carboxamide arthropodicides that are solid at room temperature) is at least about 1% of the composition by weight.

Embodiment 4A. The composition of Embodiment 4 wherein component (a) is at least about 5% of the composition by weight.

Embodiment 4B. The composition described in the Summary of the Invention or Embodiment Note 1 wherein component (a) (i.e. the one or more carboxamide arthropodicides that are solid at room temperature) does not exceed about 40% of the composition by weight.

Embodiment 4C. The composition of Embodiment 4B wherein component (a) does not exceed about 30% of the composition by weight.

Embodiment 4D. The composition of Embodiment 4C wherein component (a) does not exceed about 20% of the composition by weight.

Embodiment 4E. The composition described in the Summary of the Invention or Embodiment Note 1 wherein at least about 90% of component (a) (i.e. the one or more carboxamide arthropodicides that are solid at room temperature) is present as a suspension in an aqueous phase comprising component (c) (i.e. water).

Embodiment 4F. The composition of Embodiment 4E wherein at least about 95% of component (a) is present as a suspension in the aqueous phase.

Embodiment 4G. The composition of Embodiment 4F wherein at least about 99% of component (a) is present as a suspension in the aqueous phase.

Embodiment 4H. The composition of Embodiment 4G wherein at least about 99.8% of component (a) is present as a suspension in the aqueous phase.

Embodiment 5. The composition described in the Summary of the Invention or Embodiment Note 1 wherein component (b) (i.e. the one or more biologically active agents other than the carboxamide arthropodicides) is selected from insecticides, nematicides, bactericides, acaricides, molluscides, fungicides, herbicides, safeners, plant growth regulators and plant nutrients.

Embodiment 5A. The composition of Embodiment 5 wherein component (b) is selected from abamectin, acetamiprid, amitraz, avermectin, azadirachtin, bifenthrin, buprofezin, cartap, chlorfenapyr, chlorpyrifos, clothianidin, cyfluthrin, beta-cyfluthrin, cyhalothrin, lambda-cyhalothrin, cypermethrin, cyromazine, deltamethrin, dieldrin, dinotefuran, diofenolan, emamectin, endosulfan, esfenvalerate, ethiprole, fenothiocarb, fenoxycarb, fenvalerate, fipronil, flonicamid, flufenoxuron, hexaflumuron, hydramethylnon, imidacloprid, indoxacarb, lufenuron, metaflumizone, methomyl, methoprene, methoxyfenozide, nitenpyram, nithiazine, novaluron, oxamyl, pymetrozine, pyrethrin, pyridaben, pyridalyl, pyriproxyfen, ryanodine, spinetoram, spinosad, spirodiclofen, spiromesifen, tebufenozide, thiacloprid, thiamethoxam, thiodicarb, thiosultap-sodium, tralomethrin, triazamate, triflumuron, *Bacillus thuringiensis* subsp. *aizawai, Bacillus thuringiensis* subsp. *kurstaki*, nucleopolyhedro virus (NPV) and an encapsulated delta-endotoxin of *Bacillus thuringiensis*.

Embodiment 5B. The composition described in the Summary of the Invention or Embodiment Note 1 wherein component (b) (i.e. the one or more biologically active agents other than the carboxamide arthropodicides) is from 0 to about 20% of the composition by weight.

Embodiment 6. The composition described in the Summary of the Invention or Embodiment Note 1 wherein component (c) (i.e. the water) is from about 20 to about 60% of the composition by weight.

Embodiment 6A. The composition of Embodiment 6 wherein component (c) is from about 20 to about 50% of the composition by weight.

Embodiment 6B. The composition of Embodiment 6A wherein component (c) is from about 20 to about 40% of the composition by weight.

Embodiment 7. The composition described in the Summary of the Invention or Embodiment Note 1 wherein component (d) (i.e. one or more water-immiscible liquid compounds) is at least about 20% of the composition by weight.

Embodiment 7A. The composition of Embodiment 7 wherein component (d) is at least about 30% of the composition by weight.

Embodiment 7B. The composition described in the Summary of the Invention or Embodiment Note 1 wherein component (d) (i.e. one or more water-immiscible liquid compounds) does not exceed about 65% of the composition by weight.

Embodiment 7C. The composition of Embodiment 7B wherein component (d) does not exceed about 60% of the composition by weight.

Embodiment 7D. The composition of Embodiment 7C wherein component (d) does not exceed about 55% of the composition by weight.

Embodiment 7E. The composition of Embodiment 7D wherein component (d) does not exceed about 50% of the composition by weight.

Embodiment 8. The composition described in the Summary of the Invention or Embodiment Note 1 wherein component (d) (i.e. the one or more water-immiscible liquid compounds) comprises at least one substance selected from fatty acid esters of $C_1$-$C_4$ alkanols (including those derived from seed and fruit oils), alkoxylated fatty acid esters (including those derived from seed and fruit oils), seed and fruit oils, mineral oils, and mixtures thereof.

Embodiment 8A. The composition of Embodiment 8 wherein component (d) comprises a fatty acid ester of a $C_1$-$C_4$ alkanol or an ethoxylated fatty acid ester.

Embodiment 8B. The composition of Embodiment 8A wherein component (d) comprises a fatty acid ester of a $C_1$-$C_4$ alkanol.

Embodiment 8C. The composition of Embodiment 8B wherein component (d) comprises a $C_{10}$-$C_{22}$ fatty acid ester of a $C_1$-$C_4$ alkanol.

Embodiment 8D. The composition of Embodiment 8C wherein component (d) comprises a $C_{12}$-$C_{20}$ fatty acid ester of a $C_1$-$C_4$ alkanol.

Embodiment 8E. The composition of Embodiment 8D wherein component (d) comprises a $C_{16}$-$C_{18}$ fatty acid ester of a $C_1$-$C_4$ alkanol.

Embodiment 8F. The composition of Embodiment 8E wherein component (d) comprises a $C_{16}$-$C_{18}$ fatty acid ester of a $C_1$-$C_2$ alkanol.

Embodiment 8G. The composition of Embodiment 8F wherein component (d) comprises a $C_{16}$-$C_{18}$ fatty acid ester of methanol.

Embodiment 8H. The composition of Embodiment 8 wherein component (d) comprises a methylated seed oil of sunflower, soybean, cotton, linseed or rapeseed.

Embodiment 8I. The composition of Embodiment 8H wherein component (d) comprises a methylated seed oil of sunflower, soybean, cotton or linseed.

Embodiment 8J. The composition of Embodiment 8I wherein component (d) comprises methylated soybean oil (methyl soyate).

Embodiment 8K. The composition of Embodiment 8A wherein component (d) comprises an ethoxylated fatty acid ester.

Embodiment 8L. The composition of Embodiment 8K wherein component (d) comprises an ethoxylated seed oil of soybean, rapeseed or castor bean.

Embodiment 8M. The composition of Embodiment 8L wherein component (d) comprises an ethoxylated seed oil selected from ethoxylated soybean oil and ethoxylated castor oil.

Embodiment 8N. The composition of Embodiment 8M wherein component (d) comprises ethoxylated soybean oil.

Embodiment 8O. The composition of Embodiment 8M wherein component (d) comprises ethoxylated castor oil.

Embodiment 9. The composition described in the Summary of the Invention wherein component (e) (i.e. the surfactant component having a dispersing property) is at least about 3% of the composition by weight.

Embodiment 9A. The composition of Embodiment 9 wherein component (e) is at least about 4% of the composition by weight.

Embodiment 9B. The composition described in the Summary of the Invention wherein component (e) (i.e. the surfactant component having a dispersing property) does not exceed about 53% of the composition by weight.

Embodiment 9C. The composition of Embodiment 9B wherein component (e) does not exceed about 50% of the composition by weight.

Embodiment 9D. The composition of Embodiment 9C wherein component (e) does not exceed about 40% of the composition by weight.

Embodiment 9E. The composition of Embodiment 9D wherein component (e) does not exceed about 35% of the composition by weight.

Embodiment 9F. The composition of Embodiment 9E wherein component (e) does not exceed about 30% of the composition by weight.

Embodiment 9G. The composition of Embodiment 9F wherein component (e) does not exceed about 25% of the composition by weight.

Embodiment 9H. The composition of Embodiment 9G wherein component (e) does not exceed about 20% of the composition by weight.

Embodiment 9I. The composition of Embodiment 9H wherein component (e) does not exceed about 12% of the composition by weight.

Embodiment 10. The composition described in the Summary of the Invention wherein component (e) (i.e. the surfactant component having a dispersing property) comprises (e1) one or more surfactants having a dispersing property.

Embodiment 10A. The composition of Embodiment 10 wherein component (e1) (i.e. the one or more surfactants having a dispersing property) is from about 1 to about 10% of the composition by weight.

Embodiment 10B. The composition of Embodiment 10A wherein component (e1) is from about 1 to about 5% of the composition by weight.

Embodiment 10C. The composition described in Embodiment Note 1 wherein component (e1) (i.e. the one or more dispersing agents) is from about 1 to about 10% of the composition by weight.

Embodiment 10D. The composition of Embodiment 10C wherein component (e1) is from about 1 to about 5% of the composition by weight.

Embodiment 11. The composition described in the Summary of the Invention or Embodiment Note 1 wherein component (e) (i.e. the surfactant component having a dispersing property) or component (e1) (i.e. the one or more dispersing agents) comprises a dispersing agent selected from the class of acrylic graft copolymers having an HLB number in the range from about 10 to about 16.

Embodiment 11A. The composition of Embodiment 11 wherein component (e) or component (e1) comprises a dispersing agent selected from the class of methyl methacrylate graft copolymers having an HLB number in the range from about 10 to about 13.

Embodiment 12. The composition described in the Summary of the Invention wherein component (e) (i.e. the surfactant component having a dispersing property) comprises (e2) one or more surfactants having an emulsifying property (and thus component (e) has also an emulsifying property).

Embodiment 12A. The composition of Embodiment 12 wherein component (e2) (i.e. the one or more surfactants having an emulsifying property) is at least about 2% of the composition by weight.

Embodiment 12B. The composition of Embodiment 12A wherein component (e2) is at least about 3% of the composition by weight.

Embodiment 12C. The composition of Embodiment 12 wherein component (e2) (i.e. the one or more surfactants having an emulsifying property) does not exceed about 10% of the composition by weight.

Embodiment 12D. The composition of Embodiment 12C wherein component (e2) does not exceed about 7% of the composition by weight.

Embodiment 12E. The composition described in Embodiment Note 1 wherein component (e2) (i.e. the one or more emulsifiers) is at least about 2% of the composition by weight.

Embodiment 12F. The composition of Embodiment 12E wherein component (e2) is at least about 3% of the composition by weight.

Embodiment 12G. The composition described in the Embodiment Note 1 wherein component (e2) (i.e., the one or more emulsifiers) does not exceed about 10% of the composition by weight.

Embodiment 12H. The composition of Embodiment 12G wherein component (e2) does not exceed about 7% of the composition by weight.

Embodiment 13. The composition of Embodiment 12 wherein component (e2) (i.e. the one or more surfactants having an emulsifying property) comprises one or more surfactants selected from anionic surfactants and non-ionic surfactants, and mixtures thereof.

Embodiment 13A. The composition of Embodiment 13 wherein component (e2) is selected from anionic surfactants and non-ionic surfactants, and mixtures thereof.

Embodiment 13B. The composition described in Embodiment Note 1 wherein component (e2) (i.e. the one or more emulsifiers) is selected from anionic surfactants and non-ionic surfactants, and mixtures thereof.

Embodiment 13C. The composition of any one of Embodiments 13, 13A and 13B wherein the anionic surfactants are selected from alkylarylsulfonates (e.g., alkylbenzenesulfonates, in which the alkyl moiety may be branched or unbranched).

Embodiment 13D. The composition of Embodiment 13C wherein the anionic surfactants are selected from alkylbenzenesulfonates.

Embodiment 13E. The composition of Embodiment 13D wherein the anionic surfactants are selected from dodecylbenzenesulfonates.

Embodiment 13F. The composition of any one of Embodiments 13, 13A and 13B wherein the non-ionic surfactants are selected from ethoxylated sorbitol esters, ethoxylated sorbitan esters, ethoxylated fatty acid esters, and mixtures thereof.

Embodiment 13G. The composition of Embodiment 13F wherein the non-ionic surfactants are selected from ethoxylated sorbitol hexaoleates, ethoxylated sorbitan monooleates, ethoxylated sorbitan trioleates, ethoxylated soybean oils, ethoxylated castor oils, and mixtures thereof.

Embodiment 13H. The composition of any one of Embodiments 13, 13A and 13B wherein component (e2) comprises a mixture of non-ionic surfactants.

Embodiment 13I. The composition of Embodiment 13H wherein component (e2) comprises a mixture of an ethoxylated sorbitan monooleate and an ethoxylated soybean oil.

Embodiment 13J. The composition of any one of Embodiments 13, 13A and 13B wherein component (e2) comprises a mixture of an anionic surfactant and a non-ionic surfactant.

Embodiment 13K. The composition of Embodiment 13J wherein component (e2) comprises a mixture of a dodecylbenzenesulfonate, an ethoxylated sorbitan trioleate, an ethoxylated sorbitol hexaoleate and an ethoxylated castor oil.

Embodiment 14. The composition described in the Summary of the Invention wherein component (e) (i.e. the surfactant component having a dispersing property) comprises (e3) one or more surfactants having a wetting property (and thus component (e) has also a wetting property).

Embodiment 14A. The composition of Embodiment 14 wherein component (e3) (i.e. the one or more surfactants having a wetting property) is at least about 0.01% of the composition by weight.

Embodiment 14B. The composition of Embodiment 14 or 14A wherein component (e3) (i.e. the one or more surfactants having a wetting property) does not exceed about 15% of the composition by weight.

Embodiment 14C. The composition of Embodiment 14B wherein component (e3) does not exceed about 10% of the composition by weight.

Embodiment 14D. The composition of Embodiment 14C wherein component (e3) does not exceed about 5% of the composition by weight.

Embodiment 14E. The composition of Embodiment 14 wherein component (e3) (i.e. the one or more surfactants having a wetting property) comprises a wetting agent selected from the class of polyoxyethylene alkyl ethers.

Embodiment 14F. The composition described in Embodiment Note 1 further comprising up to about 15% by weight of component (e3) consisting of one or more wetting agents.

Embodiment 14G. The composition of 14F wherein component (e3) (i.e. the one or more wetting agents) is at least about 0.01% of the composition by weight.

Embodiment 14H. The composition of Embodiment 14F or 14G wherein component (e3) does not exceed about 10% of the composition by weight.

Embodiment 14I. The composition of Embodiment 14H wherein component (e3) does not exceed about 5% of the composition by weight.

Embodiment 14J. The composition of Embodiment 14E wherein component (e3) (i.e. the one or more wetting agents) comprises a wetting agent selected from the class of polyoxyethylene alkyl ethers.

Embodiment 15. The composition described in the Summary of the Invention wherein component (e) (i.e. the surfactant component having a dispersing property) comprises (e4) one or more surfactants having a defoaming property (and thus component (e) has also a defoaming property).

Embodiment 15A. The composition of Embodiment 15 wherein component (e4) (i.e. the one or more surfactants having a defoaming property) is at least about 0.01% of the composition by weight.

Embodiment 15B. The composition of Embodiment 15 or 15A wherein component (e4) (i.e. the one or more surfactants having a defoaming property) does not exceed about 3% of the composition by weight.

Embodiment 15C. The composition of Embodiment 15B wherein component (e4) does not exceed about 2% of the composition by weight.

Embodiment 15D. The composition of Embodiment 15C wherein component (e4) does not exceed about 1% of the composition by weight.

Embodiment 15E. The composition of Embodiment 15 wherein component (e4) (i.e. the one or more surfactants having a defoaming property) comprises a surfactant selected from silicone-based defoamers and tallow-based defoamers.

Embodiment 15F. The composition described in Embodiment Note 1 further comprising up to about 3% by weight of component (e4) consisting of one or more anti-foaming agents.

Embodiment 15G. The composition of Embodiment 15F wherein component (e4) is at least about 0.01% of the composition by weight.

Embodiment 15H. The composition of Embodiment 15F or 15G wherein component (e4) does not exceed about 2% of the composition by weight.

Embodiment 15I. The composition of Embodiment 15H wherein component (e4) does not exceed about 1% of the composition by weight.

Embodiment 15J. The composition of Embodiment 15F wherein component (e4) (i.e. the one or more anti-foaming agents) comprises an anti-foaming agent selected from silicone-based defoamers and tallow-based defoamers.

Embodiment 16. The composition described in the Summary of the Invention wherein component (e) (i.e. the surfactant component having a dispersing property) comprises one or more surfactants selected from anionic surfactants and non-ionic surfactants (including mixtures thereof) (at least one of said one or more surfactants having a dispersing property).

Embodiment 16A. The composition of Embodiment 16 wherein component (e) comprises one or more anionic surfactants selected from acrylic graft copolymers having an HLB number in the range from about 10 to about 16.

Embodiment 16B. The composition of Embodiment 16A wherein component (e) comprises one or more anionic surfactants selected from acrylic acid/methyl methacrylate graft copolymers having an HLB number in the range from about 10 to about 13.

Embodiment 16C. The composition of Embodiment 16 wherein component (e) comprises one or more anionic surfactants selected from alkylarylsulfonates (in which the alkyl moiety may be branched or unbranched).

Embodiment 16D. The composition of Embodiment 16C wherein component (e) comprises one or more anionic surfactants selected from alkylbenzenesulfonates.

Embodiment 16E. The composition of Embodiment 16D wherein component (e) comprises one or more anionic surfactants selected from dodecylbenzenesulfonates.

Embodiment 16F. The composition of Embodiment 16 wherein component (e) comprises one or more non-ionic surfactants selected from ethoxylated sorbitol esters, ethoxylated sorbitan esters and ethoxylated fatty acid esters (including mixtures thereof).

Embodiment 16G. The composition of Embodiment 16F wherein component (e) comprises one or more non-ionic surfactants selected from ethoxylated sorbitol hexaoleates, ethoxylated sorbitan monooleates, ethoxylated sorbitan trioleates and ethoxylated soybean oils, ethoxylated castor oils (including mixtures thereof).

Embodiment 16H. The composition of Embodiment 16F wherein component (e) comprises one or more non-ionic surfactants selected from ethoxylated sorbitol esters and ethoxylated sorbitan esters.

Embodiment 16I. The composition of Embodiment 16H wherein component (e) comprises one or more non-ionic surfactants selected from ethoxylated sorbitol hexaoleates, ethoxylated sorbitan monooleates and ethoxylated sorbitan trioleates.

Embodiment 16J. The composition of Embodiment 16I wherein component (e) comprises an ethoxylated sorbitol hexaoleate.

Embodiment 16K. The composition of Embodiment 16F wherein component (e) comprises one or more ethoxylated vegetable oils.

Embodiment 16L. The composition of Embodiment 16K wherein component (e) comprises one or more ethoxylated vegetable oils selected from ethoxylated soybean oils and ethoxylated castor oils.

Embodiment 16M. The composition of Embodiment 16L wherein component (e) comprises ethoxylated castor oil.

Embodiment 16N. The composition of Embodiment 16 wherein component (e) comprises a mixture of one or more anionic surfactants and one or more non-ionic surfactants.

Embodiment 16O. The composition of Embodiment 16N wherein component (e) comprises one or more anionic surfactants selected from alkylarylsulfonates and one or more non-ionic surfactants selected from the group consisting of ethoxylated sorbitol esters, ethoxylated sorbitan esters and ethoxylated fatty acid esters (including mixtures thereof).

Embodiment 16P. The composition of Embodiment 16 wherein component (e) comprises one or more non-ionic surfactants selected from polyoxyethylene alkyl ethers and polyoxyethylene/polyoxypropylene copolymers.

Embodiment 16Q. The composition of Embodiment 16P wherein component (e) comprises one or more non-ionic surfactants selected from polyoxyethylene alkyl ethers.

Embodiment 16R. The composition of Embodiment 16P wherein component (e) comprises a mixture of one or more non-ionic surfactants selected from polyoxyethylene alkyl ethers and one or more non-ionic surfactants selected from polyoxyethylene/polyoxypropylene copolymers.

Embodiment 16S. The composition of any one of Embodiments 16 and 16C through 16R wherein component (e) comprises one or more anionic surfactants selected from acrylic graft copolymers having an HLB number in the range from about 10 to about 16.

Embodiment 16T. The composition of any one of Embodiments 16 through 16S wherein component (e) comprises one or more defoamers selected from silicone-based defoamers and tallow-based defoamers.

Embodiment 17. The composition described in the Summary of the Invention or Embodiment Note 1 further comprising up to about 7% by weight of component (f) consisting of one or more antifreeze agents.

Embodiment 17A. The composition of Embodiment 17 wherein component (f) is at least about 0.01% of the composition by weight.

Embodiment 17B. The composition of Embodiment 17 or 17A wherein component (f) does not exceed about 5% of the composition by weight.

Embodiment 17C. The composition of Embodiment 17B wherein component (f) does not exceed about 4% of the composition by weight.

Embodiment 17D. The composition of Embodiment 17 wherein component (f) (i.e. the one or more antifreeze agents) comprises an antifreeze agent selected from ethylene glycol, propylene glycol, 1,3-propanediol, 1,2-propanediol, and a mixture thereof.

Embodiment 17E. The composition of Embodiment 17D wherein component (f) comprises an antifreeze agent selected from ethylene glycol, propylene glycol, and a mixture thereof.

Embodiment 18. The composition described in the Summary of the Invention or Embodiment Note 1 further comprising up to about 1% by weight of component (g) consisting of one or more preservatives (e.g., stabilizing agents and biocides).

Embodiment 18A. The composition of Embodiment 18 wherein component (g) is at least about 0.01% of the composition by weight.

Embodiment 18B. The composition of Embodiment 18 or 18A wherein component (g) does not exceed about 0.5% of the composition by weight.

Embodiment 18C. The composition of Embodiment 18B wherein component (g) does not exceed about 0.2% of the composition by weight.

Embodiment 18D. The composition of Embodiment 18 wherein component (g) comprises a biocide selected from the group consisting of formaldehyde, benzoic acid, 1,2-benzisothiazol-3(2H)-one and salts thereof.

Embodiment 18E. The composition of Embodiment 118D wherein component (g) comprises 1,2-benzisothiazol-3(2H)-one or a salt thereof.

Of note is the composition described in the Summary of the Invention or any one of Embodiments 1 through 7A and 7D through 18E wherein component (d) (i.e. the one or more water-immiscible liquid compounds) does not exceed about 60% of the composition by weight.

Also of note as embodiments are methods for preparing the arthropodicidal suspension concentrate composition, and the use of said composition for controlling arthropod pests.

Embodiments of this invention, including Embodiments 1-18E above as well as any other embodiments described herein, pertain to the compositions and methods of the present invention, which can be combined in any manner.

Examples of combinations of Embodiments 1-18E include:

Embodiment A. The composition described in the Summary of the Invention wherein component (a) (i.e. the one or more carboxamide arthropodicides that are solid at room temperature) is selected from anthranilamides of Formula 1, N-oxides, and salts thereof,

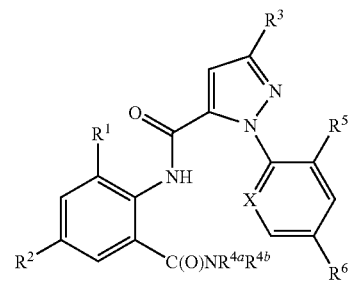

wherein
X is N, CF, CCl, CBr or CI;
$R^1$ is $CH_3$, Cl, Br or F;
$R^2$ is H, F, Cl, Br or cyano;
$R^3$ is F, Cl, Br, $C_1$-$C_4$ haloalkyl or $C_1$-$C_4$ haloalkoxy;
$R^{4a}$ is H, $C_1$-$C_4$ alkyl, cyclopropylmethyl or 1-cyclopropylethyl;
$R^{4b}$ is H or $CH_3$;
$R^5$ is H, F, Cl or Br; and
$R^6$ is H, F, Cl or Br.

Embodiment B. The composition described in the Summary of the Invention wherein component (a) (i.e. the one or more carboxamide arthropodicides that are solid at room temperature) is selected from phthalic diamides of Formula 2 and salts thereof,

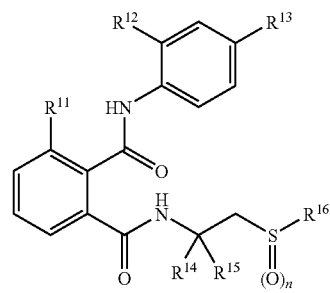

wherein
$R^{11}$ is $CH_3$, Cl, Br or I;
$R^{12}$ is $CH_3$ or Cl;
$R^{13}$ is $C_1$-$C_3$ fluoroalkyl;
$R^{14}$ is H or $CH_3$;
$R^{15}$ is H or $CH_3$;
$R^{16}$ is $C_1$-$C_2$ alkyl; and
n is 0, 1 or 2.

Embodiment C. The composition described in the Summary of the Invention or in Embodiment A or B wherein component (a) (i.e. the one or more carboxamide arthropodicides that are solid at room temperature) is from about 5 to about 40% by weight; component (b) (i.e. the one or more biologically active agents other than the carboxamide arthropodicides) is from 0 to about 20% by weight; component (c) (i.e. the water) is from about 20 to about 60% by weight; component (d) (i.e. the one or more water-immiscible liquid compounds) comprises at least one substance selected from fatty acid esters of $C_1$-$C_4$ alkanols (including those derived from seed and fruit oils), alkoxylated fatty acid esters (including those derived from seed and fruit oils), seed and fruit oils, mineral oils, and mixtures thereof, and is from about 20 to about 65% by weight; and component (e) (i.e. the surfactant component having a dispersing property) has also an emulsifying property and comprises one or more surfactants selected from anionic surfactants and non-ionic surfactants, and mixtures thereof, and is from about 3 to about 35% by weight.

Embodiment D. The composition of Embodiment C wherein component (d) comprises a $C_{16}$-$C_{18}$ fatty acid ester of a $C_1$-$C_2$ alkanol, and is from about 30 to about 60% of the composition by weight; and component (e) is from about 3 to about 12% of the composition by weight.

Embodiment E. The composition of Embodiment D wherein component (d) comprises a methylated seed oil of sunflower, soybean, cotton, linseed or rapeseed.

Embodiment F. The composition of Embodiment E wherein component (d) comprises a methylated soybean oil (i.e. methyl soyate).

Embodiment G. The composition of Embodiment D wherein component (e) comprises one or more anionic surfactants selected from acrylic graft copolymers having an HLB number in the range from about 10 to about 16.

Embodiment H. The composition of Embodiment D wherein component (e) comprises a mixture of one or more anionic surfactants selected from alkylarylsulfonates, and one or more non-ionic surfactants selected from ethoxylated sorbitol esters, ethoxylated sorbitan esters, ethoxylated fatty acid esters, and mixtures thereof.

Embodiment I. The composition of Embodiment H wherein component (e) comprises one or more anionic surfactants selected from alkylbenzenesulfonates.

Embodiment J. The composition of Embodiment H wherein component (e) comprises one or more non-ionic surfactants selected from ethoxylated sorbitol esters and ethoxylated sorbitan esters.

Embodiment K. The composition of Embodiment H wherein component (e) comprises one or more ethoxylated vegetable oils.

Embodiment L. The composition of Embodiment K wherein component (e) comprises ethoxylated castor oil.

The term "carboxamide arthropodicide that is solid at room temperature" in the present context denotes an arthropodicidal compound useful for controlling arthropod pests, having one or more carboxamide moieties and a melting point higher than about 20° C., or alternatively and typically higher than about 50° C. More typically at least one of the one or more carboxamide arthropodicides of component (a) has a melting point higher than about 80° C., even more typically above about 100° C., and most typically above about 120° C. Often all of the one or more carboxamide arthropodicides of component (a) have melting points higher than about 80° C., above about 100° C., or even above about 120° C. Typically the one or more carboxamide arthropodicides of component (a) have water solubility less than about 10 g/L and more typically less than about 5 g/L.

As is well known in the art, the term "carboxamide" refers to a moiety comprising a carbon, nitrogen and oxygen atom bonded in the configuration shown as Formula A. The carbon atom in Formula A is bonded to a carbon atom in a radical to which the carboxamide moiety is bonded. The nitrogen atom in Formula A is bonded to the carbonyl carbon of Formula A and also bonded to two other atoms, at least one atom of which is selected from a hydrogen atom or a carbon atom of another radical to which the carboxamide moiety is bonded.

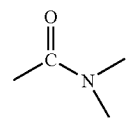

A

In one embodiment the present compositions comprise at least one carboxamide arthropodicide that is solid at room temperature and contains at least two carboxamide moieties. In another embodiment the at least one carboxamide arthropodicide contains at least two carboxamide moieties vicinally bonded to carbon atoms (i.e. in ortho arrangement) of a carbocyclic or heterocyclic ring. In a further embodiment the carbocyclic or heterocyclic ring of the at least one carboxamide arthropodicide is aromatic (i.e. satisfies the Hückel 4n+2 rule for aromaticity).

Of particular note as carboxamide arthropodicides useful in compositions of the present invention are those of Formula 1, N-oxides and salts thereof, and Formula 2 and salts thereof

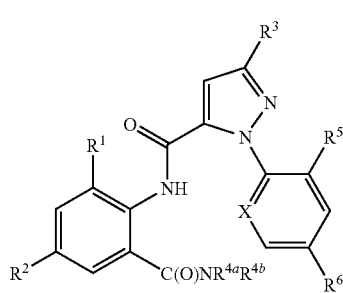

1 wherein
X is N, CF, CCl, CBr or CI;
$R^1$ is $CH_3$, Cl, Br or F;
$R^2$ is H, F, Cl, Br or cyano;
$R^3$ is F, Cl, Br, $C_1$-$C_4$ haloalkyl or $C_1$-$C_4$ haloalkoxy;
$R^{4a}$ is H, $C_1$-$C_4$ alkyl, cyclopropylmethyl or 1-cyclopropylethyl;
$R^{4b}$ is H or $CH_3$;

$R^5$ is H, F, Cl or Br; and
$R^6$ is H, F, Cl or Br.

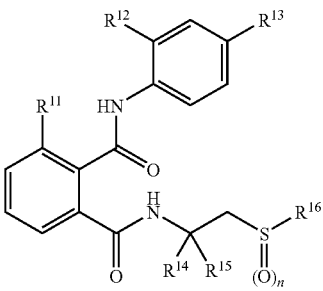

wherein
$R^{11}$ is $CH_3$, Cl, Br or I;
$R^{12}$ is $CH_3$ or Cl;
$R^{13}$ is $C_1$-$C_3$ fluoroalkyl;
$R^{14}$ is H or $CH_3$;
$R^{15}$ is H or $CH_3$;
$R^{16}$ is $C_1$-$C_2$ alkyl; and
n is 0, 1 or 2.

In the above recitations, the term "alkyl", used either alone or in compound words such as "haloalkyl" or "fluoroalkyl" includes straight-chain or branched alkyl, such as, methyl, ethyl, n-propyl, i-propyl, or the different butyl isomers. "Alkoxy" includes, for example, methoxy, ethoxy, n-propyloxy, isopropyloxy and the different butoxy isomers. The term "halogen", either alone or in compound words such as "haloalkyl", includes fluorine, chlorine, bromine or iodine. Further, when used in compound words such as "haloalkyl" or "haloalkoxy", said alkyl may be partially or fully substituted with halogen atoms which may be the same or different. Examples of "haloalkyl" include $CF_3$, $CH_2Cl$, $CH_2CF_3$ and $CCl_2CF_3$. The terms "haloalkoxy", and the like, are defined analogously to the term "haloalkyl". Examples of "haloalkoxy" include $OCF_3$, $OCH_2Cl_3$, $OCH_2CH_2CHF_2$ and $OCH_2CF_3$. "Cyclopropylmethyl" means $CH_2$ (cyclopropyl). "1-Cyclopropylethyl" means $CH(CH_3)$ (cyclopropyl).

The total number of carbon atoms in a substituent group is indicated by the "$C_i$-$C_j$" prefix where i and j are numbers from 1 to 4. For example, $C_1$-$C_4$ alkyl designates methyl through butyl, including the various isomers.

Of particular note is the composition described in the Summary of the Invention wherein component (a) (i.e. the one or more carboxamide arthropodicides that are solid at room temperature) comprises a carboxamide arthropodicide selected from the group consisting of:
3-bromo-1-(3-chloro-2-pyridinyl)-N-[4-cyano-2-methyl-6-[(methylamino)carbonyl]-phenyl]-1H-pyrazole-5-carboxamide,
3-bromo-N-[4-chloro-2-methyl-6-[(methylamino)carbonyl]phenyl]-1-(3-chloro-2-pyridinyl)-1H-pyrazole-5-carboxamide,
N-[4-chloro-2-methyl-6-[[(1-methylethyl)amino]carbonyl]phenyl]-1-(3-chloro-2-pyridinyl)-3-(trifluoromethyl)-1H-pyrazole-5-carboxamide,
N-[4-chloro-2-methyl-6-[(methylamino)carbonyl]phenyl]-1-(3-chloro-2-pyridinyl)-3-(trifluoromethyl)-1H-pyrazole-5-carboxamide,
3-bromo-N-[4-chloro-2-methyl-6-[[(1-methylethyl)amino]carbonyl]phenyl]-1-(3-chloro-2-pyridinyl)-1H-pyrazole-5-carboxamide,
1-(3-chloro-2-pyridinyl)-N-[4-cyano-2-methyl-6-[(methylamino)carbonyl]phenyl]-3-(trifluoromethyl)-1H-pyrazole-5-carboxamide,
3-bromo-1-(2-chlorophenyl)-N-[4-cyano-2-methyl-6-[[(1-methylethyl)amino]-carbonyl]-phenyl]-1H-pyrazole-5-carboxamide,
3-bromo-1-(2-chlorophenyl)-N-[4-cyano-2-methyl-6-[(methylamino)carbonyl]phenyl]-1H-pyrazole-5-carboxamide,
3-bromo-1-(2-chlorophenyl)-N-[2,4-dichloro-6-[(methylamino)carbonyl]phenyl]-1H-pyrazole-5-carboxamide,
3-bromo-N-[4-chloro-2-[[(cyclopropylmethyl)amino]carbonyl]-6-methylphenyl]-1-(3-chloro-2-pyridinyl)-1H-pyrazole-5-carboxamide,
3-bromo-1-(3-chloro-2-pyridinyl)-N-[4-cyano-2-[[(cyclopropylmethyl)amino]-carbonyl]-6-methylphenyl]-1H-pyrazole-5-carboxamide,
3-bromo-N-[4-chloro-2-[[(1-cyclopropylethyl)amino]carbonyl]-6-methylphenyl]-1-(3-chloro-2-pyridinyl)-1H-pyrazole-5-carboxamide,
3-bromo-1-(3-chloro-2-pyridinyl)-N-[4-cyano-2-[[(1-cyclopropylethyl)amino]carbonyl]-6-methylphenyl]-1H-pyrazole-5-carboxamide, and
$N^2$-[1,1-dimethyl-2-(methylsulfonyl)ethyl]-3-iodo-$N^1$-[2-methyl-4-[1,2,2,2-tetrafluoro-1-(trifluoromethyl)ethyl]phenyl]-1,2-benzenedicarboxamide.

The carboxamide arthropodicides (e.g., Formula 1) for the present compositions can also be in the form of N-oxides. One skilled in the art will appreciate that not all nitrogen-containing heterocyclic rings can form N-oxides since the nitrogen requires an available lone pair for oxidation to the oxide; one skilled in the art will recognize those nitrogen-containing heterocyclic rings which can form N-oxides. One skilled in the art will also recognize that tertiary amines can form N-oxides. Synthetic methods for the preparation of N-oxides of heterocyclic rings and tertiary amines are very well known by one skilled in the art including the oxidation of heterocyclic rings and tertiary amines with peroxy acids such as peracetic and m-chloroperbenzoic acid (MCPBA), hydrogen peroxide, alkyl hydroperoxides such as t-butyl hydroperoxide, sodium perborate, and dioxiranes such as dimethyldioxirane. These methods for the preparation of N-oxides have been extensively described and reviewed in the literature, see for example: T. L. Gilchrist in *Comprehensive Organic Synthesis*, vol. 7, pp 748-750, S. V. Ley, Ed., Pergamon Press; M. Tisler and B. Stanovnik in *Comprehensive Heterocyclic Chemistry*, vol. 3, pp 18-20, A. J. Boulton and A. McKillop, Eds., Pergamon Press; M. R. Grimmett and B. R. T. Keene in *Advances in Heterocyclic Chemistry*, vol. 43, pp 149-161, A. R. Katritzky, Ed., Academic Press; M. Tisler and B. Stanovnik in *Advances in Heterocyclic Chemistry*, vol. 9, pp 285-291, A. R. Katritzky and A. J. Boulton, Eds., Academic Press; and G. W. H. Cheeseman and E. S. G. Werstiuk in *Advances in Heterocyclic Chemistry*, vol. 22, pp 390-392, A. R. Katritzky and A. J. Boulton, Eds., Academic Press.

One skilled in the art recognizes that because in the environment and under physiological conditions salts of chemical compounds are in equilibrium with their corresponding nonsalt forms, salts share the biological utility of the nonsalt forms. Thus a wide variety of salts of carboxamide arthropodicides (e.g., Formulae 1 or 2) are useful in the present compositions (i.e. are agriculturally suitable). Such salts include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. Salts can also include those formed with organic bases (e.g., pyridine, triethylamine or ammonia) or inorganic bases (e.g., hydrides, hydroxides or carbonates of sodium, potassium, lithium, calcium, magnesium or barium) when the carboxamide arthropodicide contains an acidic moiety such as a carboxylic acid or phenol.

The composition of the invention generally comprises component (a) (i.e. the one or more carboxamide arthropodicides that are solid at room temperature) in an amount at least about 0.1% by weight, or at least about 1% by weight, or at least about 5% by weight based on the total weight of the composition. In addition, component (a) is in an amount that does not exceed about 50% by weight, or about 40% by weight, or about 30% by weight, or about 20% by weight based on the total weight of the composition. Of particular note is that the amount of component (a) is typically from about 1 to about 40%, more typically from about 5 to about 30%, and most typically from about 5 to about 20% by weight based on the total weight of the composition.

The present composition is a suspension concentrate composition comprising one or more solid carboxamide arthropodicides (i.e. component (a)) as active ingredients, which means that a substantial portion (i.e. at least half) of at least one of the carboxamide arthropodicides is suspended or dispersed as solid particles (i.e. solid particulate phase) in the composition, instead of being dissolved in the aqueous phase (i.e. the phase comprising component (c)) or water-immiscible liquid phase (i.e. the phase comprising component (d)). Typically at least about 90%, more typically at least about 95%, and most typically at least about 98% by weight of at least one of the carboxamide arthropodicides is present as solid particles instead of being dissolved. Even more typically in the present composition, at least about 90%, more typically at least about 95%, and most typically at least about 98% by weight of component (a) (i.e. the total weight of the one or more carboxamide arthropodicides) is present as solid particles instead of being dissolved.

In suspension concentrate formulations, active ingredients are in the form of small, finely distributed particles to facilitate their suspension. In the present suspension concentrate composition, the particles of component (a) are typically milled to below 10 µm in size and the median particle size is in the range between about 0.1 and 4 µm. Of note is a suspension concentrate composition of the present invention in which the median particle size is in the range between about 0.5 and about 4 µm. Of particular note is a suspension concentrate composition of the present invention wherein the particles of component (a) are milled to a median particle size in the range between about 0.1 and about 1 µm. Particularly preferred is a suspension concentrate composition wherein the particles of component (a) are milled to a median particle size in the range between about 0.1 and about 0.6 µm (i.e. the particles are "finely milled"). These finely milled carboxamide arthropodicide particles can provide increased pesticidal activity in the suspension concentrate composition of the present invention (see, for example, Test E). Particle size is the equivalent spherical diameter of the particle, i.e. the diameter of a sphere enclosing the same volume as the particle. Median particle size means that 50% of the particles have a particle size smaller than the number indicated. The particles of carboxamide arthropodicides can be suspended in the aqueous phase, the water-immiscible liquid phase, or both phases.

However, in the most typical embodiment of the present invention, the particles of component (a) are substantially suspended in the aqueous phase. Thus in this embodiment typically at least about 95%, more typically at least about 99%, and most typically at least about 99.8% of the total weight of component (a) is suspended as finely distributed particles in the aqueous phase. In this embodiment, the composition can be considered an aqueous suspension concentrate in which particles of component (a) are suspended or dispersed in the aqueous phase (as is typical for aqueous suspension concentrate formulations). In the present composition, also suspended in the aqueous phase to form an emulsion are droplets of the water-immiscible liquid phase comprising one or more water-immiscible liquid compounds (i.e. component (d)).

More than one carboxamide arthropodicide of component (a) can be present in the solid particulate phase. However, in an embodiment of the present invention, only one component (a) carboxamide arthropodicide is present in the solid particulate phase, and said carboxamide arthropodicide has a water solubility of less than about 10 g/L, or less than about 5 g/L.

In addition to component (a) (i.e. the one or more carboxamide arthropodicides solid at room temperature), the compositions of the present invention can comprise up to about 50% by weight of component (b) (i.e. the one or more biologically active agents other than the carboxamide arthropodicides). These other biologically active agents are compounds, agents or substances that differ from the component (a) carboxamide arthropodicides and can include compounds, agents or substances selected from the following classes: insecticides, fungicides, nematocides, bactericides, acaricides, herbicides, growth regulators such as rooting stimulants, chemosterilants, semiochemicals, repellents, attractants, pheromones and feeding stimulants (including both chemical and biological agents, and mixtures of several compounds, agents or substances selected from the above classes).

Compositions comprising different biologically active agents can have a broader spectrum of activity than a single agent alone. Furthermore, such mixtures can exhibit a synergistic effect. In the present invention, component (b) can exist in one or more of three phases, i.e. dissolved in the aqueous phase (i.e. the phase comprising component (c)), dissolved in the water-immiscible liquid phase (i.e. the phase comprising component (d)) or a solid particulate phase suspended or dispersed in the aqueous phase and/or the water-immiscible liquid phase. Water-soluble biologically active agents will typically be present (dissolved) predominantly in the aqueous phase, while biologically active agents of low water solubility will typically be present (dissolved) in the water-immiscible liquid phase or dispersed as a solid particulate phase distinct from the solid particulate phase containing component (a). In an embodiment of the present invention, the arthropodicidal suspension concentrate composition further comprises one other biologically active agent wherein the other biologically active agent is suspended as a particulate phase in the water-immiscible liquid phase or dissolved in the water-immiscible liquid phase.

Examples of component (b) (i.e. the one or more biologically active agents other than the carboxamide arthropodicides) are: insecticides such as abamectin, acephate, acetamiprid, acetoprole, amidoflumet (S-1955), avermectin, azadirachtin, azinphos-methyl, bifenthrin, bifenazate, bistrifluoron, buprofezin, carbofuran, cartap, chlorfenapyr, chlorfluazuron, chlorpyrifos, chlorpyrifos-methyl, chromafenozide, clothianidin, cyflumetofen, cyfluthrin, beta-cyfluthrin, cyhalothrin, gamma-cyhalothrin, lambda-cyhalothrin, cypermethrin, cyromazine, deltamethrin, diafenthiuron, diazinon, dieldrin, diflubenzuron, dimefluthrin, dimethoate, dinotefuran, diofenolan, emamectin, endosulfan, esfenvalerate, ethiprole, fenothiocarb, fenoxycarb, fenpropathrin, fenvalerate, fipronil, flonicamid flucythrinate, tau-fluvalinate, flufenerim (UR-50701), flufenoxuron, fonophos, halofenozide, hexaflumuron, hydramethylnon, imidacloprid, indoxacarb, isofenphos, lufenuron, malathion, metaflumizone, metaldehyde, methamidophos, methidathion, methomyl, methoprene, methoxychlor, metofluthrin, monocrotophos, methoxyfenozide, monocrotophos, nitenpyram, nithiazine, novaluron, noviflumuron (XDE-007), oxamyl, parathion, parathion-methyl, permethrin, phorate, phosalone, phosmet, phosphamidon, pirimicarb, profenofos, profluthrin, protrifenbute, pymetrozine, pyrafluprole, pyrethrin, pyridalyl, pyrifluquinazon, pyriprole, pyriproxyfen, rotenone, ryanodine, spinetoram, spinosad, spirodiclofen, spiromesifen (BSN 2060), spirotetramat, sulprofos, tebufenozide, teflubenzuron, tefluthrin, terbufos, tetrachlorvinphos, thiacloprid, thiamethoxam, thiodicarb, thiosultap-sodium, tolfenpyrad, tralomethrin, triazamate, trichlorfon and triflumuron; fungicides such as acibenzolar, aldimorph, amisulbrom, azaconazole, azoxystrobin, benalaxyl, benomyl, benthiavalicarb, benthiavalicarb-isopropyl, binomial, biphenyl, bitertanol, blasticidin-S, Bordeaux mixture (Tribasic copper sulfate), boscalid/nicobifen, bromuconazole, bupirimate, buthiobate, carboxin, carpropamid, captafol, captan, carbendazim, chloroneb, chlorothalonil, chlozolinate, clotrimazole, copper oxychloride, copper salts such as copper sulfate and copper hydroxide, cyazofamid, cyflufenamid, cymoxanil, cyproconazole, cyprodinil, dichlofluanid, diclocymet, diclomezine, dicloran, diethofencarb, difenoconazole, dimethomorph, dimoxystrobin, diniconazole, diniconazole-M, dinocap, discostrobin, dithianon, dodemorph, dodine, econazole, etaconazole, edifenphos, epoxiconazole, ethaboxam, ethirimol, etridiazole, famoxadone, fenamidone, fenarimol, fenbuconazole, fencaramid, fenfuram, fenhexamid, fenoxanil, fenpiclonil, fenpropidin, fenpropimorph, fentin acetate, fentin hydroxide, ferbam, ferimzone, fluazinam, fludioxonil, flumetover, fluopicolide, fluoxastrobin, fluquinconazole, fluquinconazole, flusilazole, flusulfamide, flutolanil, flutriafol, folpet, fosetyl-aluminum, fuberidazole, furalaxyl, furametapyr, hexaconazole, hymexazol, guazatine, imazalil, imibenconazole, iminoctadine, ipconazole, iprobenfos, iprodione, iprovalicarb, isoconazole, isoprothiolane, kasugamycin, kresoxim-methyl, mancozeb, mandipropamid, maneb, mefenoxam, mepanipyrim, mepronil, metalaxyl, metconazole, methasulfocarb, metiram, metominostrobin/fenominostrobin, metrafenone, miconazole, myclobutanil, neo-asozin (ferric methanearsonate), nuarimol, octhilinone, ofurace, orysastrobin, oxadixyl, oxolinic acid, oxpoconazole, oxycarboxin, paclobutrazol, penconazole, pencycuron, penthiopyrad, perfurazoate, phosphonic acid, phthalide, picobenzamid, picoxystrobin, polyoxins, probenazole, prochloraz, procymidone, propamocarb, propamocarb-hydrochloride, propiconazole, propineb, proquinazid, prothioconazole, pyraclostrobin, pyrazophos, pyrifenox, pyrimethanil, pyrifenox, pyrrolnitrin, pyroquilon, quinconazole, quinoxyfen, quintozene, silthiofam, simeconazole, spiroxamine, streptomycin, sulfur, tebuconazole, tecloftalam, tecnazene, tetraconazole, thiabendazole, thifluzamide, thiophanate, thiophanate-methyl, thiram, tiadinil, tolclofos-methyl, tolyfluanid, triadimefon, triadimenol, triarimol, triazoxide, tridemorph, trimorphamid, tricyclazole, trifloxystrobin, triforine, triticonazole, uniconazole, validamycin, vinclozolin, zineb, ziram, and zoxamide; nematocides such as aldicarb, imicyafos, oxamyl and fenamiphos; bactericides such as streptomycin; acaricides such as amitraz, chinomethionat, chlorbenzilate, cyhexatin, dicofol, dienochlor, etoxazole, fenazaquin, fenbutatin oxide, fenpropathrin, fenpyroximate, hexythiazox, propargite, pyridaben and tebufenpyrad; and biological agents including entomopathogenic bacteria, such as *Bacillus thuringiensis* subsp. *aizawai*, *Bacillus thuringiensis* subsp. *kurstaki*, and the encapsulated delta-endotoxins of *Bacillus thuringiensis* (e.g., Cellcap, MPV, MPVII); entomopathogenic fungi, such as green muscardine fungus; and entomopathogenic virus including baculovirus, nucleopolyhedro virus (NPV) such as HzNPV, AfNPV; and granulosis virus (GV) such as CpGV.

General references for these agricultural protectants (i.e. insecticides, nematocides, acaricides and biological agents) include *The Pesticide Manual*, 13th Edition, C. D. S. Tomlin, Ed., British Crop Protection Council, Farnham, Surrey, U.K., 2003 and *The BioPesticide Manual*, $2^{nd}$ Edition, L. G. Copping, Ed., British Crop Protection Council, Farnham, Surrey, U.K., 2001.

Of note is a composition of the present invention wherein component (b) (i.e. the one or more biologically active agents other than the carboxamide arthropodicides) comprises a biologically active agent selected from the group consisting of abamectin, acephate, acetamiprid, acetoprole, aldicarb, amidoflumet, amitraz, avermectin, azadirachtin, azinphos-methyl, bifenthrin, bifenazate, bistrifluoron, buprofezin, carbofuran, cartap, chinomethionat, chlorfenapyr, chlorfluazuron, chlorpyrifos, chlorpyrifos-methyl, chlorobenzilate, chromafenozide, clothianidin, cyflumetofen, cyfluthrin, beta-cyfluthrin, cyhalothrin, gamma-cyhalothrin, lambda-cyhalothrin, cyhexatin, cypermethrin, cyromazine, deltamethrin, diafenthiuron, diazinon, dicofol, dieldrin, dienochlor, diflubenzuron, dimefluthrin, dimethoate, dinotefuran, diofenolan, emamectin, endosulfan, esfenvalerate, ethiprole, etoxazole, fenamiphos, fenazaquin, fenbutatin oxide, fenothiocarb, fenoxycarb, fenpropathrin, fenpyroximate, fenvalerate, fipronil, flonicamid, flucythrinate, tau-fluvalinate, flufenerim, flufenoxuron, fonophos, halofenozide, hexaflumuron, hexythiazox, hydramethylnon, imicyafos, imidacloprid, indoxacarb, isofenphos, lufenuron, malathion, metaflumizone, metaldehyde, methamidophos, methidathion, methomyl, methoprene, methoxychlor, methoxyfenozide, metofluthrin, monocrotophos, nitenpyram, nithiazine, novaluron, noviflumuron, oxamyl, parathion, parathion-methyl, permethrin, phorate, phosalone, phosmet, phosphamidon, pirimicarb, profenofos, profluthrin, propargite, protrifenbute, pymetrozine, pyrafluprole, pyrethrin, pyridaben, pyridalyl, pyrifluquinazon, pyriprole, pyriproxyfen, rotenone, ryanodine, spinetoram, spinosad, spiridiclofen, spiromesifen (BSN 2060), spirotetramat, sulprofos, tebufenozide, tebufenpyrad, teflubenzuron, tefluthrin, terbufos, tetrachlorvinphos, thiacloprid, thiamethoxam, thiodicarb, thiosultap-sodium, tolfenpyrad, tralomethrin, triazamate, trichlorfon, triflumuron, *Bacillus thuringiensis* subsp. *aizawai*, *Bacillus thuringiensis* subsp. *kurstaki*, nucleopolyhedro virus, an encapsulated delta-endotoxin of *Bacillus thuringiensis*, baculovirus, entomopathogenic bacteria, entomopathogenic virus and entomopathogenic fungi.

Of further note in the present invention are arthropodicidal suspension concentrate compositions wherein component (b) (i.e. the one or more biologically active agents other than the carboxamide arthropodicides) comprises a biologically active agent selected from abamectin, acetamiprid, amitraz, avermectin, azadirachtin, bifenthrin, buprofezin, cartap, chlorfenapyr, chlorpyrifos, clothianidin, cyfluthrin, beta-cyfluthrin, cyhalothrin, lambda-cyhalothrin, cypermethrin, cyromazine, deltamethrin, dieldrin, dinotefuran, diofenolan, emamectin, endosulfan, esfenvalerate, ethiprole, fenothiocarb, fenoxycarb, fenvalerate, fipronil, flonicamid, flufenoxuron, hexaflumuron, hydramethylnon, imidacloprid, indoxacarb, lufenuron, metaflumizone, methomyl, methoprene, methoxyfenozide, nitenpyram, nithiazine, novaluron, oxamyl, pymetrozine, pyrethrin, pyridaben, pyridalyl, pyriproxyfen, ryanodine, spinetoram, spinosad, spirodiclofen, spiromesifen, tebufenozide, thiacloprid, thiamethoxam, thiodicarb, thiosultap-sodium, tralomethrin, triazamate, triflumuron, *Bacillus thuringiensis* subsp. *aizawai*, *Bacillus thuringiensis* subsp. *kurstaki*, nucleopolyhedro virus and an encapsulated delta-endotoxin of *Bacillus thuringiensis*.

Of particular note in the present invention are arthropodicidal suspension concentrate compositions wherein component (b) comprises an insecticide or an acaricide including sodium channel modulators such as bifenthrin, cypermethrin, cyhalothrin, lambda-cyhalothrin, cyfluthrin, beta-cyfluthrin, deltamethrin, dimefluthrin, esfenvalerate, fenvalerate, indoxacarb, metofluthrin, profluthrin, pyrethrin and tralomethrin; cholinesterase inhibitors such as chlorpyrifos, methomyl, oxamyl, thiodicarb and triazamate; neonicotinoids such as acetamiprid, clothianidin, dinotefuran, imidacloprid, nitenpyram, nithiazine, thiacloprid and thiamethoxam; insecticidal macrocyclic lactones such as spinetoram, spinosad, abamectin, avermectin and emamectin; GABA (γ-aminobutyric acid)-regulated chloride channel blockers such as endosulfan, ethiprole and fipronil; chitin synthesis inhibitors such as buprofezin, cyromazine, flufenoxuron, hexaflumuron, lufenuron, novaluron, noviflumuron and triflumuron; juvenile hormone mimics such as diofenolan, fenoxycarb, methoprene and pyriproxyfen; octopamine receptor ligands such as amitraz; ecdysone agonists such as azadirachtin, methoxyfenozide and tebufenozide; ryanodine receptor ligands such as ryanodine; nereistoxin analogs such as cartap; mitochondrial electron transport inhibitors such as chlorfenapyr, hydramethylnon and pyridaben; lipid biosynthesis inhibitors such as spirodiclofen and spiromesifen; cyclodiene insecticides such as dieldrin; cyflumetofen; fenothiocarb; flonicamid; metaflumizone; pyrafluprole; pyridalyl; pyriprole; pymetrozine; spirotetramat; and thiosultap-sodium. One embodiment of the at least one other biologically active agent for mixing with the at least one carboxamide arthropodicide in the compositions of this invention includes nucleopolyhedro virus (NPV) such as *Helicoverpa zea* nuclear polyhedrosis virus (HzNPV) and *Anagrapha falcifera* nuclear polyhedrosis virus (AfNPV); *Bacillus thuringiensis* and encapsulated delta-endotoxins of *Bacillus thuringiensis* such as Cellcap, MPV and MPVII; as well as naturally occurring and genetically modified viral insecticides including members of the family Baculoviridae as well as entomophagous fungi.

The compositions of the present invention can comprise in addition to component (a) (i.e. the one or more carboxamide arthropodicides) up to about 50%, or up to about 20% by weight of component (b) (i.e. the one or more biologically active agents other than the carboxamide arthropodicides). Of note are compositions of the invention wherein the weight ratio of component (b) to component (a) ranges from about 1:100 to about 100:1.

Component (c) (i.e. the water) of the present composition provides a continuous liquid phase in which the active ingredient (e.g., component (a) and optionally component (b)) as solid particles and the water-immiscible liquid as droplets (emulsion) are dispersed. Typically the water is present in an amount of from about 20 to about 70% by weight, more typically from about 20 to about 60% by weight, most typically from about 20 to about 50% by weight, or about 20 to about 40% by weight based on the total weight of the composition.

For a conventional aqueous suspension concentrate composition typically at least one thickener such as a fumed silica or gum is needed to prevent undesirable phase separation and/or sedimentation of solid particles that usually occurs during storage in unstructured suspension concentrates. To prepare such aqueous suspension concentrate compositions, high-shear milling is required to reduce the particle size of the undissolved solid active ingredients (e.g., component (a) and optionally component (b)). However, high-shear milling generally results in degradation of thickeners such as fumed silica or gums. Therefore, a skilled artisan would prepare the suspension concentrate compositions without the thickeners in a first mixing and high-shear milling cycle, then after milling the thickeners would be added with a second round of mixing. This mixing after milling requires additional equipment (e.g., tanks, charging stations and low-shear mixers) and makes the manufacturing process more complicated and costly.

In the present compositions, the finely dispersed water-immiscible liquid droplets comprising component (d) (i.e. the one or more water-immiscible liquid compounds) were discovered to not only provide adequate structure stability similar to a thickener but also maintain the ability to thicken even after high-shear mixing. Using component (d) as a thickener instead of conventional thickeners allows elimination of the costly transfer of the composition to a low-shear mixer to add the thickener.

In order for component (d) to function as a thickener in the present invention, the amount of component (d) as well as its droplet size in the suspension concentrate are important factors for building cohesive structure in the composition. Through simple experimentation the amount of component (d) can be optimized with respect to the amounts of active ingredients (e.g., component (a) and optionally component (b)) and other components to achieve the desired thickening effect. At lower than optimal concentration, component (d) may not provide sufficient structure stability to prevent phase separation and/or particle sedimentation, while at higher than optimal concentration, the suspension concentrate can become too thick to pour.

Of note is a composition of the present invention comprising component (d) in an amount typically from about 10 to about 60% by weight, more typically from about 20 to about 55% by weight, and most typically from about 30 to about 50% by weight based on the total weight of the composition.

Smaller size of the water-immiscible liquid droplets comprising component (d) results in better structure building in the suspension concentrate. Component (d) in the composition of the present invention is homogeneously dispersed in the aqueous phase in the form of droplets of a size typically ranging from about 0.1 to about 10 μm. Droplet size is the equivalent spherical diameter of the droplet, i.e. the diameter of a sphere enclosing the same volume as the droplet. Water is the continuous liquid carrier of the present composition, but component (d) may also serve as a carrier for ingredients such as, for example, adjuvants including emulsifiers, other additives such as safeners, and optionally component (b).

The term "water-immiscible liquid compound" as used herein refers to a compound that is liquid at 20° C. and is soluble in water to an extent less than about 2% by weight at 20° C. Of note are compositions of the present invention wherein component (d) is soluble in water to an extent of less than about 0.1%, or less than about 0.01%, or less than about 0.001% by weight at 20° C. Low solubility of liquid compounds in water is a result of low molecular polarity. As the low molecular polarity of water-immiscible liquid compounds is closer than the high polarity of water to the polarity of carboxamide arthropodicides, carboxamide arthropodicides generally are more soluble in water-immiscible liquid compounds than in water, in which they have little solubility. Nevertheless a large amount of component (a) (i.e. the one or more carboxamide arthropodicides) relative to the amount of component (d) (i.e. the one or more water-immiscible liquid compounds) typically results in most of the component (a) being present as solid particles instead of dissolved in component (d) of the present compositions. In one embodiment of the present composition, component (d) has a viscosity below 50 cP at 20° C. (which can facilitate pourability of the composition), and in another embodiment of the present composition, component (d) has a flash point above 65° C. and/or low toxicity (both properties having potential safety benefits).

For certain embodiments of the composition of the present invention, component (d) comprises a water-immiscible liquid compound which is selected from fatty acid esters of $C_1$-$C_4$ alkanols, alkoxylated fatty acid esters, vegetable oils and mineral oils. (However, unless alkoxylated fatty acid esters predominate (i.e. exceed by weight the total amount of other water-immiscible liquid compounds) these alkoxylated fatty acid esters are regarded to be part of the surfactant component (e) and not component (d) in the context of the present invention.) Not only do these particular water-immiscible liquid compounds have low polarity and work well in the present compositions, but they are relatively nontoxic and are readily available from commercial sources at moderate cost.

Mineral oils, also known as liquid petrolatum, liquid paraffin, paraffin oil and paraffinic oil, comprise mixtures of long-chain, liquid hydrocarbons obtained from petroleum. Mineral oils can be obtained commercially from many sources, either as a straight mineral oil or blended with emulsifiers, for example, Isopar® H (Deutsche Exxon Chemicals) or Suremix® (DuPont, USA).

Vegetable oils are oils obtained from plants. Vegetable oils are typically obtained by pressing or solvent extracting seeds (e.g., sunflower, rapeseed, soybean, corn (maize), linseed (flax)) or fruits (e.g., olive). Examples of vegetable oils that are commercially available at moderate cost are sunflower oil, rapeseed oil, canola oil, soybean oil and corn oil. Vegetable oil mostly comprises fatty acid glycerides, i.e. glycerol esters of fatty acids.

Fatty acid esters of $C_1$-$C_4$ alkanols (i.e. fatty acids esterified with $C_1$-$C_4$ alkanols instead of glycerol) have lower viscosities than vegetable oils and can be particularly useful as water-immiscible liquid compounds for the present compositions.

The fatty acid portions of the fatty acid esters consist of a carboxylate moiety bound to a hydrocarbon chain, which can be unbranched or branched, but are typically unbranched in natural sources. The hydrocarbon chain can be saturated or unsaturated; typically the hydrocarbon chain is saturated (i.e. alkyl) or contains 1 or 2 carbon-carbon double bonds (i.e. alkenyl). Fatty acid esters formed from fatty acids containing either an odd number of carbon atoms (i.e. even number of carbon atoms in the hydrocarbon chain) or an even number of carbon atoms (i.e. odd number of carbon atoms in the hydrocarbon chain) are useful in the compositions of the present invention. Although esters of lower fatty acids (e.g., containing as few as 4 carbon atoms) can be included in the present compositions, they can be mixed with esters of higher fatty acids to decrease polarity, water solubility and volatility. Esters of fatty acids having at least 10 carbon atoms typically have favorable physical properties. As fatty acids obtained from natural sources typically contain an even number of carbon atoms ranging from 10 to 22 carbon atoms, alkanol esters of these fatty acids are of note for reasons of commercial availability and cost. The $C_{10}$-$C_{22}$ fatty acid esters with an even number of carbon atoms are, for example, erucic acid, lauric acid, palmitic acid, stearic acid, oleic acid, linoleic acid and linolenic acid. Of note are one or more fatty acid esters in the compositions of the present invention which comprise esters of fatty acids containing 12 to 20 carbon atoms. Of further note are one or more fatty acid esters in the compositions of the present invention which comprise esters of fatty acids containing 16 to 18 carbon atoms.

The $C_1$-$C_4$ alkanol-derived portions of the fatty acid esters can be unbranched (i.e. straight-chain) or branched, but are typically unbranched. For reasons including favorable physical properties, commercial availability and cost, of note are the fatty acid esters which are fatty acids esterified with $C_1$-$C_2$ alkanols and particularly $C_1$ alkanol (i.e. methanol). The fatty acid alkanol esters in a composition of the present invention can also be derived from a mixture of alcohols (e.g., methanol and ethanol).

Fatty acid compositions obtained from natural sources (e.g., seed oils) typically consist of fatty acids having a range of chain lengths and different degrees of unsaturation. Fatty acid ester compositions derived from such fatty acid mixtures can be useful in the compositions of the present invention without need to first separate the fatty acid esters. Suitable fatty acid ester compositions obtained from plants include seed and fruit oils of sunflower, rapeseed, olive, corn, soybean, cotton and linseed. Of note is a composition of the invention wherein component (d) comprises fatty acid methyl esters derived from seed oils of sunflower, soybean, cotton, linseed or rapeseed, or more particularly sunflower, soybean, cotton or linseed. Of particular note is a composition of the invention wherein component (d) comprises fatty acid methyl esters derived from soybean oil (also known as methylated soybean oil or methyl soyate).

Fatty acid esters of alkanols and methods for their preparation are well known in the art. For example, "biodiesel" typically comprises fatty acid esters of ethanol or more commonly methanol. Two principal routes used to prepare fatty acid alkanol esters are transesterification starting with another fatty acid ester (often a naturally occurring ester with glycerol) and direct esterification starting with the fatty acid. A variety of methods are known for these routes. For example, direct esterification can be accomplished by contacting a fatty acid with an alkanol in the presence of a strong acid catalyst such as sulfuric acid. Transesterification can be accomplished by contacting a starting fatty acid ester with the alcohol in the presence of a strong acid catalyst such as sulfuric acid but more commonly a strong base such as sodium hydroxide.

Alkylated seed oils are the transesterification products of seed oils with an alkanol. For example methylated soybean oil, also known as methyl soyate, comprises methyl esters produced by the transesterification of soybean oil with methanol. Methyl soyate thus comprises methyl esters of fatty acids in the approximate molar ratio that the fatty acids occur esterified with glycerol in soybean seed oil. Alkylated seed oils such as methyl soyate can be distilled to modify the proportion of methyl fatty acid esters.

Alkoxylated fatty acid esters, including alkoxylated fatty acid glycerides (also known as alkoxylated triglycerides) are often regarded as "semi-natural" surfactants as they are made from alkoxylation (ethoxylation or propoxylation) of fatty acid esters of natural origin such as vegetable oil (e.g., a seed oil). Common alkoxylated fatty acid esters prepared from vegetable oils include ethoxylated fatty acid esters containing 10 to 60 ethylene oxide units. For example, POE 25 castor oil, POE 30 soybean oil and POE 30 rapeseed oil are particularly useful as component (d).

The present composition includes from about 1 to about 55% by weight of (e) a surfactant component having a dispersing property. Surfactants (also known as "surface-active agents") generally modify, and most often reduce, the surface tension of a liquid. Depending on the nature of the hydrophilic and lipophilic groups in a surfactant molecule, surfactants can be useful as wetting agents, dispersing agents (i.e. dispersants), emulsifiers or anti-foaming agents (i.e. defoamers). Surfactants are described as anionic, non-ionic or cationic surfactants based on the chemical nature of their hydrophilic groups. Typical surfactants are described in *McCutcheon's Detergents and Emulsifiers Annual*, Allured Publ. Corp., Ridgewood, N.J., as well as Sisely and Wood, *Encyclopedia of Surface Active Agents*, Chemical Publ. Co., Inc., New York, 1964.

An anionic surfactant is a surface-active molecule in which the hydrophilic group connected to the lipophilic portion of the molecule forms a negative ion (i.e. anion) when placed in aqueous solution. Carboxylate, sulfate, sulfonate and phosphate are the hydrophilic groups commonly found in anionic surfactants. Examples of anionic surfactants include sodium alkylnaphthalene sulfonates, naphthalenesulfonate formaldehyde condensates, alkylbenzenesulfonates, lignin sulfonates, alkyl sulfates, alkyl ether sulfates, dialkyl sulfosuccinates, N,N-dialkyltaurates, polycarboxylates, phosphate esters, ethoxylated tristyrylphenol phosphate salts and alkali salts of fatty acids.

A non-ionic surfactant is a surface-active molecule that does not contain ionizable polar end groups but does contain hydrophilic and lipophilic portions. Examples of non-ionic surfactants include ethoxylated alcohols, ethoxylated alkylphenols, ethoxylated sorbitol esters, ethoxylated fatty acid esters, polyoxyethylene/polyoxypropylene block copolymers, glycerol esters, and alkylpolyglycosides where the number of glucose units, referred to as degree of polymerization (D.P.), can range from 1 to 3 and the alkyl units can range from $C_6$ to $C_{14}$ (see *Pure and Applied Chemistry* 72, 1255-1264). As is well known in the art, in these surfactants "ethoxylated" refers to the presence of chains comprising one or more oxyethylene units ($-OCH_2CH_2-$) formed by reaction of ethylene oxide with hydroxyl groups on the sorbitan, sorbitol or fatty acid components, respectively. In ethoxylated sorbitan esters and ethoxylated sorbitol esters, the hydroxyl groups present after ethoxylation are esterified. If more than one oxyethylene unit is generally present on each surfactant molecule, "polyoxyethylene" can be included in the surfactant name, or alternatively a POE (polyoxyethylene) number can be included in the name to indicate the average number of oxyethylene units per molecule.

A cationic surfactant is a surface-active molecule in which the hydrophilic group connected to the lipophilic portion of the molecule forms a positive ion (i.e. cation) when placed in aqueous solution. Examples of cationic surfactants include quaternary ammonium salts such as ethoxylated fatty amines, benzylalkylammonium salts, pyridinium salts and quaternary imidazolium compounds.

The ability of surfactants to reduce surface tension depends upon the molecular structure of the surfactant. In particular, the balance of lipophilic to hydrophilic groups influences whether the surfactant is soluble in water and whether water-immiscible liquid droplets can be stabilized (e.g., emulsified) in water. The HLB number of a surfactant indicates the polarity of the molecules in an arbitrary range of 1 to 40, with the most commonly used surfactants having a value between 1 and 20. The number increases with increasing hydrophilicity. Surfactants with HLB numbers between 0 and 7 are considered lipophilic, surfactants with HLB numbers between 12 and 20 are considered hydrophilic, and surfactants with HLB numbers between 7 and 12 are considered intermediate.

Examples of hydrophilic surfactants include sodium, calcium and isopropylamine salts of branched or linear alkylbenzenesulfonates. Non-ionic surfactants such as ethoxylated castor oil, ethoxylated sorbitan oleates, ethoxylated alkyl phenols and ethoxylated fatty acids can be in the intermediate HLB range, depending upon chain length and degree of ethoxylation. Triesters of oleic acid and sorbitan (i.e. sorbitan trioleate) and triesters of stearic acid and sorbitan (i.e. sorbitan tristearate) are examples of lipophilic surfactants. Lists of surfactants and their respective HLB numbers have been published widely, for example in A. W. Adamson, *Physical Chemistry of Surfaces*, John Wiley and Sons, 1982.

In the present disclosure and claims, the terms "dispersing agent", "dispersant" and "dispersing property" particularly relate to ability to disperse solid particles in an aqueous medium. The terms "dispersing agent" and "dispersant" mean a surfactant having a dispersing property. In contrast, the terms "emulsifying agent", "emulsifier" and "emulsifying property" particularly relate to ability to disperse liquid droplets in an aqueous medium. The terms "emulsifying agent" and "emulsifier" mean a surfactant having an emulsifying property. Similarly, the term "wetting agent" means a surfactant having a wetting property, and the term "anti-foaming agent" means a surfactant having a defoaming property.

In a suspension concentrate composition, when solids in the particulate phase come close to each other and their mutual attraction overcomes repulsive forces, recombination can occur and the particles can stick together either by flocculation or by agglomeration. Dispersing agents, also called dispersants, can be absorbed on the particle surface to create either an electrostatic and/or steric barrier between particles, thus reducing particle-to-particle interaction and stabilizing the suspension.

Therefore the present composition includes (e) a surfactant component having a dispersing property to disperse particles of solids including component (a) and any solids from component (b) in the aqueous phase. To provide the required dispersing property the surfactant component (e) comprises (e1) one or more surfactants having a dispersing property, i.e. one or more dispersing agents. In the present composition, component (e1) (i.e. the one or more surfactants having a dispersing property, also known as dispersing agents) is added in an amount typically from about 1% to about 15% by weight, more typically from 1% to about 10% by weight, and most typically from 1% to about 5% by weight based on the total weight of the composition to help stabilize the suspension of solids including component (a) and any solids from component (b) in the aqueous phase.

Examples of dispersing agents include anionic surfactants such as phosphate esters of tristyrylphenol ethoxylates (e.g., Soprophor® 3D33), alkylarylsulfonic acids and their salts (e.g., Supragil® MNS90), lignin sulfonates (e.g., ammonium lignosulfonate or sodium lignosulfonate), polyphenol sulfonates, and polyacrylic acids and acrylic graft copolymers such as acrylic acid/methyl methacrylate/polyethylene glycol graft copolymers (e.g., Atlox® 4913) and their salts; and non-ionic surfactants such as fatty alcohol ethers, polyoxyethylene/polyoxypropylene block copolymers (e.g., Pluronic® F108 polyoxyethylene/polyoxypropylene block copolymer) and other polyoxyalkylene-containing polymers such as Atlox® 4912 (block copolymer of poly(ethylene glycol) and hydroxystearic acid; MW approximately 5000) and Atlas™ G-5000 (poly(alkylene glycol) ether). One skilled in the art recognizes the terms "polyoxyethylene", "poly(ethylene glycol)" and "poly(ethylene oxide)" are essentially synonyms corresponding to a "$-O-[CH_2CH_2O]_n-$" polymeric chain.

In one embodiment of the present invention, component (e1) (i.e. the one or more dispersing agents) comprises an anionic polymeric surfactant, in particular, an acrylic graft copolymer having an HLB number of around 10 to 16. In another embodiment, component (e1) comprises a methacrylic acid/methyl methacrylate/polyethylene glycol graft copolymer having an HLB number of around 10 to 13, for example Atlox® 4913 (HLB 12), which is commercially available from Croda.

In addition to solid particles suspended in the aqueous phase of the present composition, liquid droplets comprising component (d) (i.e. one or more water-immiscible liquid compounds) are suspended in the aqueous phase. For many embodiments of component (d), one or more emulsifiers are needed in the compositions of this invention to maintain component (d) as finely dispersed droplets. Under these circumstances component (e) (i.e. the surfactant component having a dispersing property) also has an emulsifying property, and thus the surfactant component has both dispersing and emulsifying properties. However, in certain embodiments of the composition of the invention, component (d) (i.e. the one and more water-immiscible liquid compounds) has self-emulsifying capability, for example, when component (d) comprises ethoxylated fatty acid esters such as ethoxylated soybean oil (POE 20-30), and then component (e) (i.e. the surfactant component having a dispersing property) does not need to have an emulsifying property to provide stable suspension concentrates. Under these circumstances an emulsifying property is optional for surfactant component (e), and this component can be described as a surfactant component having a dispersing property and optionally an emulsifying property.

To provide an emulsifying property the surfactant component (e) comprises (e2) one or more surfactants having an emulsifying property, i.e. one or more emulsifiers. Surfactants that are useful as emulsifiers typically reside at the oil-water interface with their lipophilic portion immersed in the water-immiscible liquid droplets and their hydrophilic portion penetrating the surrounding aqueous phase, thereby causing reduction of surface tension. Emulsifiers can prevent the coalescence of water-immiscible liquid droplets in water and thus help maintain stable dispersions of water-immiscible liquid droplets in aqueous phase, which are known as emulsions.

In the context of the present composition, the emulsifiers can facilitate the formation of dispersions of droplets comprising component (d) and other oil-soluble components such as component (b) in the continuous aqueous phase. The presence of solid particles of component (a) and optionally component (b) and other water-insoluble components may significantly influence the emulsion capability of a certain emulsifier. Therefore stable emulsions comprising small water-immiscible liquid droplets can be obtained by matching empirically the HLB number of the emulsifiers to the one or more water-immiscible liquid compounds and the dispersed solid particles in the composition. Furthermore, the emulsifiers may help dispersion of the suspension concentrate composition when it is diluted with water, for example, forming a spray tank mixture before a spray application.

The composition of the present invention generally comprises component (e2) (i.e. the one or more surfactants having an emulsifying property, also known as emulsifiers) in an amount from about 0 to about 20% by weight, more typically from about 2 to about 10% by weight, and most typically from about 3 to about 7% by weight based on the total weight of the composition.

While achieving best results for a particular combination of components (e.g., components (a) and (d), and optionally (b)) may involve adjusting the relative amount of component (e2), optimal results for compositions of the present invention are typically achieved from an emulsifier or a mixture of emulsifiers constituting component (e2) having HLB numbers in the range of about 8 to about 15, and more particularly in the range from about 8 to about 12.

A skilled artisan knows that mixtures of emulsifiers can be used to facilitate adjusting overall HLB to provide optimal performance. The HLB number of an emulsifier mixture is calculated as the sum of the products of the mass fraction of each emulsifier component multiplied by its respective HLB number. For example, a 6:4 mixture of a POE 30 castor oil (HLB 11.8) with an ethoxylated sorbitol hexaoleate (HLB 10.5) would have a HLB number of 11.3. Adding a sorbitan monolaurate (HLB 8.6) to a level of 30% and reducing the ethoxylated sorbitol hexaoleate to 20%, with the remainder being the POE 30 castor oil (i.e. 50%), would reduce the HLB number of the emulsifier mixture to 10.6.

In one embodiment of the compositions of the present invention, component (e2) (i.e. the one or more emulsifiers) is selected from an anionic surfactant and a non-ionic surfactant.

For reasons including favorable physical properties, commercial availability and cost, of note are anionic surfactants selected from linear (unbranched) alkylbenzenesulfonates and branched alkylbenzenesulfonates. Of particular note are anionic surfactants that are linear alkylbenzenesulfonates. Of further note are compositions of the present invention wherein component (e2) comprises at least one anionic surfactant in the class of dodecylbenzenesulfonates, for example, calcium dodecylbenzenesulfonate (e.g., Rhodacal® 70/B (Rhodia) or Phenylsulfonat® CA100 (Clariant)) or isopropylammonium dodecyl-benzenesulfonate (e.g., Atlox® 3300B (Croda)).

For reasons including favorable physical properties, commercial availability and cost, of note are non-ionic surfactants selected from ethoxylated sorbitan esters, ethoxylated sorbitol esters, ethoxylated fatty acid esters (including ethoxylated triglycerides), and mixtures thereof. Ethoxylated sorbitan esters of note are ethoxylated sorbitan oleate (e.g., monooleate, trioleate), ethoxylated sorbitan laurate (i.e. trilaurate), each having 10-30 oxyethylene units (i.e. POE 10 to POE 30). Ethoxylated sorbitol esters of note are ethoxylated sorbitol oleate (i.e. hexaoleate), ethoxylated sorbitol laurate (i.e. hexylaurate). Ethoxylated fatty acid esters of note are ethoxylated seed oils such as ethoxylated soybean oil, ethoxylated castor oil and ethoxylated rapeseed oil, each having 10-30 oxyethylene units (i.e. POE 10 to POE 30). Of note are compositions of the present invention wherein component (e2) comprises at least one non-ionic surfactant selected from ethoxylated sorbitan esters (e.g., POE 20 sorbitan trioleate, POE 20 sorbitan monooleate), ethoxylated sorbitol esters (e.g., POE 40 sorbitol hexaoleate), and ethoxylated vegetable (e.g., seed) oils (e.g., POE 30 (ethoxylated) soybean oil, POE 25 (ethoxylated) castor oil, POE 30 (ethoxylated) rapeseed oil). Of further note are compositions of the present invention wherein component (e2) comprises a mixture of ethoxylated sorbitan monooleate and ethoxylated soybean oil wherein the weight ratio of the ethoxylated sorbitan monooleate to the ethoxylated soybean oil ranges from about 3:1 to about 1:1. Examples of suitable non-ionic surfactants include Emsorb™ 6900 (Cognis) POE 20 sorbitan monooleate, Tween® 80 (Croda) POE 20 sorbitan monooleate, Cirresol® G-1086 (Croda) POE 40 sorbitol hexaoleate, Agnique® SBO-30 (Cognis) POE 30 ethoxylated soybean oil and Trylox® 5904 (Cognis) POE 25 ethoxylated castor oil. Of the ethoxylated vegetable oils, ethoxylated castor oil is particularly useful as a constituent of components (e) and (e2) according to the present invention.

In the present composition the surfactants forming component (e) typically partition between the aqueous phase comprising component (c) (i.e. water) and the water-immiscible liquid comprising component (d) (i.e. the one or more water-immiscible liquid compounds). Therefore the aqueous phase aqueous phase also comprises one or more dispersing agents (i.e. component (e1)) to facilitate dispersion of the suspended particles of component (a), and the water-immiscible liquid phase may also comprise one or more emulsifiers (i.e., component (e2)), which are needed to form an emulsion of the water-immiscible liquid phase in the aqueous phase if component (d) (i.e. the one or more water-immiscible liquid compounds) is not self-emulsifying.

One skilled in the art will appreciate that while formulating ingredients typically predominate in a particular phase, lesser amounts may be present in other phases. Thus while emulsifiers (i.e. component (e2)) typically predominate in the water-immiscible liquid phase rather than the aqueous phase, their emulsifying effect results from their presence at the interface between the water-immiscible liquid phase droplets and the aqueous phase, and depending upon their molecular properties, significant amounts of emulsifiers may be present in the aqueous phase. Also, while dispersants (i.e. component (e1)) typically predominate in the aqueous phase, depending upon their molecular properties, significant amounts of dispersants may be present in the water-immiscible liquid phase. Furthermore, minor amounts (e.g., less than about 2% by weight at 20° C.) of water may be present in the water-immiscible phase, and minor amounts (e.g., less than about 2% by weight at 20° C.) of water-immiscible compounds may be present in the aqueous phase.

Component (e) (i.e. the surfactant component having a dispersing property) may also have a wetting property. To provide a wetting property the surfactant component (e) comprises (e3) one or more surfactants having a wetting property (i.e. wetting agents). Wetting agents are surfactants capable of lowering the surface tension of liquids and facilitating the wetting of surfaces of solid particles and the penetration of liquids into the capillaries of particles.

Examples of wetting agents include alkyl sulfate salts (e.g., sodium lauryl sulfate, Sipon™ LC 98), alkyl ether sulfate salts (e.g., sodium ether lauryl sulfate, Supralate™ ME), alkylarylsulfonates (i.e. salts of alkylarylsulfonic acids, including arylsulfonic acids substituted with more than one alkyl moiety) such as sodium or calcium alkylbenzenesulfonates (e.g., Rhodacal® DS1) and alkylnaphthalenesulfonates (e.g., Rhodacal® BX-78), α-olefin sulfonate salts, sulfonyl succinate salts, salts of polycarboxylic acids, ethoxylated fatty alcohols, ethoxylated fatty acids, ethoxylated fatty amines, ethoxylated substituted phenols such as alkylphenols or arylphenols, ethoxylated alkyl ethers and polyoxyethylene/polyoxypropylene block copolymers.

Of note is a composition of the invention wherein component (e3) (i.e. the one or more wetting agents) comprises one or more wetting agents selected from the classes of ethoxylated alkyl ethers and polyoxyethylene/polyoxypropylene block copolymers, particularly the class of ethoxylated alkyl ethers, such as Synperonic® A7. Of particular note is a composition comprising a mixture of one or more wetting agents selected from ethoxylated alkyl ethers with one or more wetting agents selected from polyoxyethylene/polyoxypropylene block copolymers, such as Atlox® 4894 (Croda).

When component (e3) (i.e. the one or more wetting agents) is present, it typically amounts to at least about 0.01% of the composition by weight. Component (e3) does not exceed typically about 15%, more typically about 10% and most typically about 5% of the total weight of the composition.

Component (e) (i.e. the surfactant component having a dispersing property) may also have a defoaming property. To provide a defoaming property the surfactant component (e) comprises (e4) one or more surfactants having a defoaming property (i.e. anti-foaming agents).

Anti-foaming agents are surfactants that can effectively either prevent foam formation or reduce or eliminate it once it has formed. Because anti-foaming agents typically are insoluble in water, they are generally sold commercially as solutions or emulsions (which contain water and a surfactant as well as the anti-foaming agents), which disperse as tiny droplets upon addition to an aqueous medium.

Examples of anti-foaming agents include silicone oils, mineral oils, polydialkylsiloxanes such as polydimethylsiloxanes, alkyne diols (e.g., Surfynol® 104), fluoroaliphatic esters or perfluoroalkylphosphonic or perfluoroalkylphosphinic acids or salts thereof. Of note is a composition of the invention wherein component (e4) (i.e. the one or more anti-foaming agents) comprises an anti-foaming agent selected from silicone-based defoamers such as Agnique® DMF111S (Croda) and tallow-based defoamers such as Agnique® Soap L (Croda).

When component (e4) (i.e. the one or more anti-foaming agents) is present, it typically amounts to at least about 0.01% of the composition by weight. Component (e4) does not exceed typically about 3%, more typically about 2% and most typically about 1% of the total weight of the composition.

The compositions of the present invention may also comprise other auxiliaries such as anti-freeze agents, preservatives such as chemical stabilizers or biocides, viscosity controlling agents and fertilizers. The suspension concentrate compositions of this invention typically further comprise (f) from 0 to about 7% of one or more antifreeze agents; and (g) from 0 to about 1% of one or more preservatives (e.g., stabilizing agents and biocides).

Examples of antifreeze agents include glycols such as ethylene glycol, diethylene glycol, propylene glycol, dipropylene glycol, glycerin, 1,3-propanediol, 1,2-propanediol, or polyethylene glycol of molecular weight in the range from about 200 to about 1000. Suitable antifreeze agents for the composition of the present invention include ethylene glycol, propylene glycol, glycerin, 1,3-propanediol and 1,2-propanediol.

For reasons including commercial availability and cost, of note is a composition of the invention wherein component (f) (i.e. the one or more antifreeze agents) comprises an anti-freeze agent selected from ethylene glycol, propylene glycol, 1,3-propanediol and 1,2-propanediol. Of particular note is a composition of the invention wherein component (f) comprises ethylene glycol or propylene glycol.

When component (f) (i.e. the one or more antifreeze agents) is present, it typically amounts to at least about 0.01% of the composition by weight. Typically component (f) does not exceed about 7%, more typically about 5% and most typically about 3% of the total weight of the composition. Of note are compositions of the invention wherein the weight ratio of component (f) to component (c) ranges from 1:5 to 1:20.

Component (g) (i.e. the one or more preservatives) of the present composition comprises stabilizing agents and biocides. Stabilizing agents can prevent decomposition of active ingredients (i.e. component (a) and/or component (b)) during storage, for example, anti-oxidants (such as butylhydroxytoluene) or pH modifiers (such as citric acid or acetic acid). Biocides can prevent or reduce microbial contamination within a formulated composition. Particular suitable biocides are bactericides such as Legend™ MK (mixture of 5-chloro-2-methyl-3(2H)-isothiazolone with 2-methyl-3(2H)-isothiazolone), EDTA (ethylenediaminetetraacetic acid), formaldehyde, benzoic acid, or 1,2-benzisothiazol-3(2H)-one or its salts, e.g., Proxel® BD or Proxel® GXL (Arch). Of note is the present composition wherein component (g) comprises a biocide, in particular, a bactericide such as 1,2-benzisothiazol-3(2H)-one or one of its salts.

When component (g) (i.e. the one or more preservatives) is present, it typically amounts to at least about 0.01% of the composition by weight. Component (g) does not exceed typically about 1%, more typically about 0.5% and most typically about 0.3% of the total weight of the composition.

Other formulation ingredients can be used in the present invention such as rheology modifiers, dyes, and the like. These ingredients are known to one skilled in the art and can be found described, for example, in *McCutcheon's, Volume 2: Functional Materials* published by MC Publishing Company annually.

To prepare a composition of the present invention, typically an aqueous suspension not including component (d) (i.e. the one or more water-immiscible compounds) and any component (e2) (i.e. the emulsifier) used in the composition is first prepared. Methods for making suspensions and dispersions of particles are well known and include ball-milling, bead-milling, sand-milling, colloid milling and air-milling combined with high-speed blending, which typically involves high shear. Then the water-immiscible phase (i.e., component (d) and any component (e2) used in the composition) is added to the aqueous suspension using high-speed (i.e. high shear) blending to form an emulsion of water-immiscible liquid droplets in the aqueous phase. The aqueous phase thus functions as a continuous liquid medium for both dispersed particles of component (a) and also emulsified droplets comprising component (d), both the dispersed particles and emulsified droplets typically being smaller than about 10 µm.

The desired method for applying the diluted compositions of the present invention, such as spraying, atomizing, dispersing or pouring, will depend on the desired objectives and the given circumstances, and can be readily determined by one skilled in the art. Although the arthropodicidal suspension concentrate composition of the present invention can be applied directly to an arthropod pest or its environment, the arthropodicidal suspension concentrate composition is ordinarily first diluted with water to form a diluted composition, and then the arthropod pest or its environment is contacted with an effective amount of the diluted composition to control the arthropod pest. After mixing with water, the resulting diluted composition formed from the arthropodicidal suspension concentrate typically comprises an emulsion of droplets of the one or more water-immiscible liquid compounds and a suspension of solid particles of the one or more carboxamide arthropodicides. This diluted composition can be applied to an arthropod pest or its environment by a variety of means including spraying. The present arthropodicidal suspension concentrate compositions after dilution with water, spraying and then drying have been discovered to provide remarkably effective control of arthropod pests (e.g., killing the pests, interfering with their growth development or reproduction, and/or inhibiting their feeding) that is resistant to subsequent wash-off (e.g., on exposure to rain).

To supplement the adjuvants contained in pesticide formulations, separately formulated adjuvant products can be added to spray tank mixtures. These additional adjuvants are commonly known as "spray adjuvants" or "tank-mix adjuvants", and include any substance mixed in a spray tank to improve the performance of a pesticide treatment, such as by enhancing efficacy (e.g., biological availability, adhesion, penetration, uniformity of coverage and durability of protection), or minimizing or eliminating spray application problems associated with incompatibility, foaming, drift, evaporation, volatilization and degradation. As no single adjuvant generally can provide all these benefits, compatible adjuvants are often combined to perform multiple functions. To obtain optimal performance, adjuvants are selected with regard to the properties of the active ingredient, formulation and target (e.g., crops, arthropod pests).

Among the spray adjuvants, oils including crop oils, crop oil concentrates, vegetable oil concentrates and methylated seed oil concentrates are used to improve the efficacy of pesticides, possibly by means of promoting more even and uniform spray deposits. Products identified as "crop oil" typically contain 95 to 98% paraffin or naphtha-based petroleum oil and 1 to 2% of one or more surfactants functioning as emulsifiers. Products identified as "crop oil concentrates" typically consist of 80 to 85% of emulsifiable petroleum-based oil and 15 to 20% of non-ionic surfactants. Products correctly identified as "vegetable oil concentrates" typically consist of 80 to 85% of vegetable oil (i.e. seed or fruit oil, most commonly from cotton, linseed, soybean or sunflower) and 15 to 20% of non-ionic surfactants. Adjuvant performance can be improved by replacing the vegetable oil with methyl esters of fatty acids that are typically derived from vegetable oils. Examples of methylated seed oil concentrates include MSO® Concentrate from UAP-Loveland Products, Inc. and Premium MSO Methylated Spray Oil from Helena Chemical Company. The amount of oil-based adjuvants added to spray mixtures generally does not exceed about 2.5% by volume, and more typically the amount is from about 0.1 to about 1% by volume. The application rates of oil-based adjuvants added to spray mixtures are typically between about 1 to about 5 L per hectare, and methylated seed oil-based adjuvants in particular are typically used at a rate from about 1 to about 2.5 L per hectare.

Spray adjuvants containing oils, with or without emulsifiers, particularly methylated seed oils, are compatible in tank mixtures with the present arthropodicidal suspension concentrate compositions. Furthermore, spray mixtures comprising added methylated seed oils (e.g., methyl soyate) even without emulsifiers in admixture with the present compositions are found to provide remarkably improved control efficacy on certain arthropod pests (such as for protecting plants from such arthropod pests). Therefore one embodiment of the present invention relates to a method for controlling an arthropod pest, comprising diluting an arthropodicidal suspension concentrate composition of the present invention with water, and optionally adding an adjuvant such as a methylated seed oil (in any order of addition or mixing) to form a diluted composition, and contacting the arthropod pest or its environment with an effective amount of said diluted composition.

The ratio of the volume of arthropodicidal suspension concentrate composition to the volume of water used to dilute it is generally in the range from about 1:100 to about 1:1000, more typically from about 1:200 to about 1:800, and most typically from about 1:300 to about 1:600. The amount of diluted composition needed for effective control of an arthropod pest depends upon a variety of factors including the concentration of the one or more carboxamide arthropodicides and any other arthropodicides in the arthropodicidal suspension concentrate composition, the extent of dilution in water, the susceptibility of the arthropod pest to the one or more carboxamide arthropodicides and any other arthropodicides and environmental conditions as well as the concentration of other adjuvants, but can be easily determined by calculation and simple experimentation by one skilled in the art.

Without further elaboration, it is believed that one skilled in the art using the preceding description can utilize the present invention to its fullest extent. The following Examples are, therefore, to be construed as merely illustrative and not limiting of the disclosure in any way whatsoever.

General Procedure for Preparing a Suspension Concentrate Composition

Table 1 lists chemical identities for the ingredients, and Tables 2A and 2B list amounts used in the compositions of Examples A-E and Comparative Examples A and B. The following general procedure was used for the preparation of suspension concentrate compositions of Examples A-C and E.

In a 250-mL stainless steel beaker equipped with an overhead stirrer, water (c), a carboxamide arthropodicide (a), dispersing agents (f) and other ingredients including wetting agents (g), anti-foaming agents (h), anti-freeze agents (i) and preservatives (j) (as specified for each Example) were mixed with stirring to make an aqueous mixture. The mixture was homogenized using a rotor stator mixer (Polytron PT 3000, Kinematica AG, Switzerland) to provide about 8-9 micron median particle size, and then milled to about 1 micron median particle size using a 50 mL Eiger Motormill (a horizontal bead mill manufactured by Eiger Machinery Inc., Chicago, Ill.) to afford a aqueous suspension concentrate. Particle size distribution of the compositions were measured by light scattering analysis using a Malvern Mastersizer® S (Malvern Instruments, Malvern, Worcestershire, UK). The one or more water-immiscible liquid compounds (d) and emulsifiers (e2) (as specified for each Example) were then blended with the aqueous suspension concentrate under high shear with a rotary speed of at least 1000 rpm using a rotor stator mixer (Polytron PT 3000, Kinematica AG, Switzerland) to provide a composition of the present invention.

For the preparation of finely milled Example D, the aqueous suspension concentrate containing components (a), (c), and (f)-(j) was prepared as described above and was further milled (approximately doubling the total milling time) to provide a smaller particle size before the addition of components (d) and (e).

Comparative Examples A and B, which are aqueous suspension concentrates, were prepared by mixing the components as specified in Table 2B (except the thickener) and milling using the method described previously for Examples A, B and C. The thickener(s) was hydrated in water, then mixed with the aqueous mixture under agitation, and then milled in a single passage at high flow rate (2L/minute) and low mill speed (10 m/s) (i.e. low shear) to form the comparative aqueous suspension concentrate.

The sample of Compound 1 used in the present Examples and Comparative Examples was prepared as described in Reference Example 1.

REFERENCE EXAMPLE 1

Preparation of 3-bromo-1-(3-chloro-2-pyridinyl)-N-[4-cyano-2-methyl-6-[(methylamino)carbonyl]phenyl]-1H-pyrazole-5-carboxamide To a mixture of 3-bromo-1-(3-chloro-2-pyridinyl)-1H-pyrazole-5-carboxylic acid (20.6 kg) and 2-amino-5-cyano-N,3-dimethylbenzamide (14.1 kg) in acetonitrile (114 kg) was added 3-picoline (22.2 kg). The mixture was cooled to −10 to −14° C., and then methanesulfonyl chloride (10.6 kg) was slowly added so that the temperature did not exceed 5° C. After reaction completion as ascertained by HPLC and NMR analyses, the mixture was worked up by successively adding water (72.6 kg) and concentrated hydrochloric acid (7.94 kg) at such a rate that the temperature did not exceed 5° C. After being maintained at a temperature not exceeding 5° C. for about 30 minutes, the reaction mixture was filtered to collect the solid product, which was successively washed with acetonitrile-water (2:1, 2×12.3 kg) and acetonitrile (2×10.4 kg). The solid was then dried at about 50° C. under reduced pressure and a flow of nitrogen gas to give the title product as a white crystalline solid, which was directly used in the present formulation Examples and Comparative Examples. With a moderate rate of heating (heating to about 150° C. over 5 minutes and then decreasing rate of heating from about 4-5° C./minute to about 3° C./minute to reach 210° C. over about 15 minutes more) to facilitate volatilization of loosely entrained solvents from the solid product, melting occurred in the range between 204 and 210° C.

TABLE 1

Identity of Ingredients used in Examples

| Name | Identity |
|---|---|
| Compound 1 | 3-Bromo-1-(3-chloro-2-pyridinyl)-N-[4-cyano-2-methyl-6-[(methylamino)carbonyl]phenyl]-1H-pyrazole-5-carboxamide |
| Agnique ® ME 18SDU (Cognis Corp) | Methylated soybean oil |
| Cirrasol ® G-1086 (Croda) | POE 40 sorbitol hexaoleate |
| Agnique ® BL2707 (Cognis Corp) | Mixture of Ca dodecylbenzenesulfonate & POE 30 castor oil |
| Atlox ® 4913 (Croda) | Methacrylic acid/methyl methacrylate/polyethylene glycol graft copolymer |
| Atlox ® 4894 (Croda) | Mixture of polyoxyethylene alkyl ether and polyoxyethylene/polyoxypropylene block copolymer |
| Agnique ® DFM111S (Cognis Corp) | Dimethyl silicone |
| Proxel ® GXL (Arch) | Sodium 1,2-benzisothiazol-3(2H)-one |
| Legend ® MK (Rohm & Haas) | Mixture of 5-chloro-2-methyl-4-isothiazolin-3-one and 2-methyl-4-isothiazolon-3-one |
| Rhodopol ® 23 (Rhodia) | Heteropolysaccharides, Xanthan gum |
| Acti-Gel ® 208 (Active Minerals) | Hydrous alumina silicate |

TABLE 2A

Compositions of Examples of the Present Invention.

| Component (Note 1) | Ingredient | Example A | Example B | Example C | Example D | Example E |
|---|---|---|---|---|---|---|
| (a) carboxamide arthropodicide | Compound 1 | 10.0 | 10.53 | 21.05 | 5.35 | 5.26 |
| (c) water | water | 30.0 | 29.21 | 30.0 | 30 | 30 |
| (d) water-immiscible liquid compounds | Agnique ® ME 18SDU | 45.9 | 47.14 | 36.72 | 53.23 | 53.15 |
| (e1) dispersing agents | Atlox 4913 | 3.0 | 2.92 | 3.0 | 1.5 | 1.5 |
| (e2) emulsifiers | Agnique ® BL2707 | 3.8 | 3.8 | 2.9 | 4.4 | 4.4 |
| (e2) emulsifiers | Cirresol ® G-1086 | 0.77 | 0.94 | 0.73 | 0.89 | 0.89 |
| (e3) wetting agents | Atlox ® 4894 | 2.0 | 1.95 | 2.0 | 1.0 | 1.0 |
| (e4) anti-foaming agents | Agnique ® DPMI US | 0.5 | 0.49 | 0.5 | 0.5 | 0.5 |
| (f) antifreeze agents | Propylene Glycol | 3.0 | 2.92 | 3.0 | 3.0 | 3.0 |
| (g) preservatives | Proxel ® GXL | 0.1 | 0.1 | 0.1 | 0.1 | 0.1 |

Amounts are by weight percent based on total weight of the composition.
(Note 1):
The Component column in Table 2A lists the principal function, preceded by the component designation defined in the Summary of Invention and Embodiments, intended for each ingredient in the Example compositions. However, the ingredients may also have other functional properties in the Example compositions.

TABLE 2B

Compositions of Comparative Examples.

| Component (Note 2) | Ingredient | Comparative Example A | Comparative Example B |
|---|---|---|---|
| (a) carboxamide arthropodicide | Compound 1 | 19.7 | 20.0 |
| (c) water | water | 66.1 | 66.35 |
| (e1) dispersing agents | Atlox ® 4913 | 3.0 | 3.0 |
| (e3) wetting agents | Atlox ® 4894 | 2.0 | 2.0 |
| (e4) anti-foaming agents | Agnique ® DFM111S | 0.5 | 0.5 |
| (f) antifreeze agents | Propylene Glycol | 6.8 | 6.8 |
| (g) preservatives | Legend ® MK | 0.1 | — |
| (g) preservatives | Proxel ® GXL | — | 0.1 |
| Thickeners | Rhodopol ® 23 | 0.8 | 0.25 |
| Anti-gel agents | Acti-Gel ® 208 | 1.0 | 1.0 |

Amounts are by weight percent based on total weight of the composition.
(Note 2):
The Component column in Table 2B lists the principal function, preceded by the component designation defined in the Summary of Invention and Embodiments, intended for each ingredient in the Comparative Example compositions. However, the ingredients may also have other functional properties in the Comparative Example compositions. The Comparative Example compositions lack Component (d) (i.e. one or more water-immiscible compounds) forming an aqueous emulsion required for a composition of the present invention.

Evaluation of Chemical and Physical Stability of Suspension Concentrates

The chemical stability of each Example was evaluated by aging samples in heated ovens (i.e. at 54° C. for 2 weeks) and then comparing the content of the carboxamide arthropodicide before and after aging. Carboxamide arthropodicide content was determined by assaying the compositions with high-pressure liquid chromatography (HPLC) using reverse phase columns. The percent relative decomposition was calculated by subtracting the final weight percent of carboxamide arthropodicide from the initial weight percent of carboxamide arthropodicide, then dividing the difference by the initial weight percent of carboxamide arthropodicide, and then multiplying the resulting quotient by 100%.

The physical stability of each suspension concentrate Example was determined by measuring the extent of phase separation of the oven-aged samples. The degree of phase separation was determined by measuring with a ruler the thickness of the separated layer devoid of suspended particles and the total height of the liquid composition in the sample bottle, and then dividing the thickness of the separated layer by the total height of the liquid composition, and multiplying the quotient by 100%. If the interface between the separated phases was not even, several measurements were made and the results averaged. For an aqueous suspension composition comprising an emulsion of a water-immiscible liquid, the separated layer is usually on top of the liquid composition. The separated layer typically comprises water-insoluble materials including the water-immiscible liquid compounds and/or emulsifiers. Table 3 lists results from the chemical stability and physical stability evaluations.

TABLE 3

Chemical and Physical Stabilities of Compositions Prepared

| | % Relative Decomposition | % Phase Separation |
|---|---|---|
| Example A | 0.85 | 0.0 |
| Comparative Example A | 1.2 | — |

Example A, which comprised no conventional thickener at all, but instead 45.9% of water-immiscible liquid compound emulsified in the aqueous phase, showed chemical stability comparable to Comparative Example A.

The phase separation results listed in Table 3 indicate the water-immiscible liquid compounds and emulsifiers effectively provided a stable suspension structure for Example A, a composition of the present invention. Comparative Example A having 0.8% of thickener (Rhodopol® 23) and no water-immiscible ingredients is expected to not be subject to phase separation, and thus was not tested for phase separation.

Biological Examples of the Invention

Test A

For evaluating control of silverleaf whitefly (*Bemisia argentifolii* Bellows & Perring), the test unit consisted of a 14-21-day-old cotton plant with at least two true leaves, which was planted in Redi-earth® medium (Scotts Co.). The plants were placed in screened cages, where whitefly adults were introduced and allowed to lay eggs for approximately twenty-four hours. Only plants showing egg lay were used for testing. Before spraying the test solutions, the plants were checked again for egg hatch and crawler settlement. One leaf per plant was considered as one replication; four replications were used per treatment.

All formulated materials were diluted with water to make test mixtures at four different concentrations. Plants were sprayed using a TeeJet flat fan spray nozzle positioned 7.5 inches (19 cm) above the tallest plant. Spray flow rate was adjusted to 5.5 mL/sec for an equivalent of 500 L/ha. After spraying, plants were allowed to dry in a ventilated enclosure and held for six days in a growth chamber at 50% relative humidity, 16 h with light (as daytime) at 28° C. and 8 h in dark (as nighttime) at 24° C. After removing all leaves from each test plant, evaluation was made by counting dead and live nymphs present on the underside of the leaves.

Using the collected data, the mean concentrations killing 50% or 90% of the population (mean $LC_{50}$ or $LC_{90}$) were calculated and are listed in Table 4.

TABLE 4 mean $LC_{50}$ and $LC_{90}$ of Silverleaf Whitefly

| | Mean $LC_{50}$ (g a.i. g/ha) | Mean $LC_{90}$ (g a.i. g/ha) |
|---|---|---|
| Example B | 230 | 434 |
| Example C | 1003 | 4940 |
| Comparative Example B | 1904 | 19012 |

The results indicate that the compositions of Examples B and C of the present invention showed enhanced efficacy as compared to the composition of Comparative Example B for controlling silverleaf whitefly.

Test B

For evaluating rainfastness (resistance to wash-off) for the control of beet armyworm (*Spodoptera exigua*), the test unit consisted of a cotton plant grown in a pot containing Redi-earth® medium. Test solutions were formulated as described in TEST A. When the plants were at the 4-6 true leaf growth stage, the plants were sprayed with the formulated test solution using a belt sprayer with nozzle positioned 19 cm above the plants and providing an application volume of 234 liters/ha. All formulated materials were diluted with water to make test mixtures at four different concentrations. After spraying of the formulated test mixtures, each test unit was allowed to dry for 2 h and then exposed to about 95 mm of simulated rain in a greenhouse. Plants were then allowed to dry, and leaves were cut and placed on agar in 16-cell plastic trays. One 3-day-old, laboratory reared beet armyworm larva was placed in each cell, and the cells were covered with a plastic lid. Two 16-cell trays were used per treatment. Trays were held in a growth chamber at 75% relative humidity, 16 h with light (as daytime) and 8 h in dark (as nighttime) at 25° C. Four days after infestation, each test unit was evaluated for larvae mortality, and the mean concentrations killing 50% or 90% of the population (mean $LC_{50}$ or $LC_{90}$) were calculated and are listed in Table 5.

TABLE 5

Mean $LC_{50}$ and $LC_{90}$ of Beet Armyworm with exposure to simulated rain.

| Composition | Mean $LC_{50}$ (g a.i./ha) | Mean $LC_{90}$ (g a.i./ha) |
|---|---|---|
| Example B | 15 | 36 |
| Comparative Example B | 60 | 195 |

Test results in Table 5 demonstrate that Example B, a composition of the present invention, showed markedly 4-fold enhanced efficacy after exposure to simulated rain compared to Comparative Example B ($LC_{50}$ 15 vs. 60) for controlling beet armyworm. The difference was even more dramatic for the $LC_{90}$, which showed Example B is at least 5-fold more potent than the Comparative Example B.

These results suggest that the compositions of the present invention have much better rainfastness and resistance to wash-off compared to aqueous suspension concentrate compositions that do not include components (d) and (e2). The rainfastness and wash-off resistance of the present compositions makes these compositions particularly useful for controlling arthropod pests in crop fields, orchards and other areas subject to rainfall.

Test C

To evaluate the effect of methylated seed oil as an adjuvant for the present composition for controlling silverleaf whitefly (*Bemisia argentifolii*), this test was conducted according to the method described in TEST A.

Example B or Comparative Example B was diluted with water to provide a spray mixture containing the active ingredient (Compound 1) and methylated soybean oil (also known as methyl soyate, obtained from Cognis). Concentrations of the active ingredient and the methylated spray oil are as specified in Table 6.

The mean concentrations killing 50% of the population (mean $LC_{50}$) were calculated and are also listed in Table 6.

TABLE 6

Mean $LC_{50}$ of Silverleaf Whitefly

| | Concentration of a.i. g/ha | Water-immiscible liquid in formulation (ppm) | Methyl soyate added (ppm) | Total Water-immiscible liquid (ppm) | % Mean Mortality | $LC_{50}$ (g a.i./ha) |
|---|---|---|---|---|---|---|
| Comparative Example B | $LC_{50}$ obtained from TEST A, see Table 4 | | | | | 1904 |
| | 18 | 0 | 1202 | 1202 | 6 | 55 |
| | 35 | 0 | 1404 | 1404 | 23 | |
| | 70 | 0 | 1808 | 1808 | 62 | |

TABLE 6-continued

Mean LC$_{50}$ of Silverleaf Whitefly

|  | Concentration of a.i. g/ha | Water-immiscible liquid in formulation (ppm) | Methyl soyate added (ppm) | Total Water-immiscible liquid (ppm) | % Mean Mortality | LC$_{50}$ (g a.i./ha) |
|---|---|---|---|---|---|---|
| Example B |  | LC$_{50}$ obtained from TEST A, see Table 4 | | | | 230 |
|  | 18 | 172 | 1030 | 1202 | 13 | 38 |
|  | 35 | 344 | 1060 | 1404 | 35 |  |
|  | 70 | 689 | 1119 | 1808 | 88 |  |
| Methyl soyate |  | 0 | 0 | 1808 | 1808 | 0 |
| Untreated |  | 0 | 0 | 0 | 0 | 0 |

* LC$_{50}$ is determined by running Logit/Probit dose response/mortality regression analysis and significance of the LC$_{50}$ is determined by overlapping 95% confidence intervals.

The data demonstrate that the addition of the methyl soyate as a spray tank mixture with both Example B and Comparative Example B compositions increased potency (i.e. lowering the LC$_{50}$). Furthermore, with the same amount of active ingredient and total amount of methyl soyate at each active ingredient concentration, Example B consistently showed better control in terms of higher % of mortality as compared to Comparative Example B. These results suggest that the superior biological performance of the compositions of the present invention is not solely contributed by the water-immiscible liquid compound.

Test D

To evaluate the effect of additional methylated seed oil as an adjuvant for the present composition for controlling silverleaf whitefly (*Bemisia argentifolii*), this test was conducted according to the method described in TEST A.

The composition of Example B or Example E was diluted with water to provide a spray mixture containing the active ingredient (Compound 1, component (a)) and methylated soybean oil (also known as methyl soyate, obtained from Cognis, component (d)). Concentrations of the active ingredient component (a) and the methylated soybean oil component (d) are as specified in Table 2A.

Using the collected data, the mean concentrations killing 50% or 90% of the population (mean LC$_{50}$ or LC$_{90}$) were calculated and are listed in Table 7.

TABLE 7

Mean LC$_{50}$ and LC$_{90}$ of Silverleaf Whitefly

|  | Mean LC$_{50}$ (g a.i./ha) | Mean LC$_{90}$ (g a.i./ha) |
|---|---|---|
| Example B (10.53% component (a), 47.14% component (d)) | 113 | 233 |
| Example E (5.26% component (a), 53.15% component (d)) | 77 | 147 |

The results indicate that the composition of Example E of the present invention, which contained 6% by weight more of methyl soyate and 50% less of the active ingredient as compared to the composition of Example B, showed enhanced efficacy of the active ingredient as compared to the composition of Example B for controlling silverleaf whitefly.

Test E

To evaluate the effect of component (a) particle size for the present composition for controlling silverleaf whitefly (*Bemisia argentifolii*), this test was conducted according to the method described in TEST A.

Example E was diluted with water to provide a spray mixture containing the active ingredient (Compound 1) and methylated soybean oil (also known as methyl soyate, obtained from Cognis). The finely milled composition of Example D was then diluted with water to provide a spray mixture containing the active ingredient (Compound 1) and methylated soybean oil. Concentrations of the active ingredient and the methylated spray oil are as specified in Table 2A.

Using the collected data, the mean concentrations killing 50% or 90% of the population (mean LC$_{50}$ or LC$_{90}$) were calculated and are listed in Table 8.

TABLE 8

Mean LC$_{50}$ and LC$_{90}$ of Silverleaf Whitefly

|  | Mean LC$_{50}$ (g a.i./ha) | Mean LC$_{90}$ (g a.i./ha) |
|---|---|---|
| Example E (standard milling) | 77 | 147 |
| Example D (finely milled) | 21 | 53 |

The results indicate that the finely milled composition of Example D of the present invention showed significantly increased pesticidal activity for controlling silverleaf whitefly as compared to the composition of Example E.

What is claimed is:

1. An arthropodicidal suspension concentrate composition comprising by weight based on the total weight of the composition:
   (a) from 5 to about 30% of one or more carboxamide arthropodicides that are solid at room temperature selected from anthranilamides of Formula 1, N-oxides, and salts thereof, wherein
   X is N, CF, CCl, CBr or CI;
   $R^1$ is CH$_3$, Cl, Br or F;
   $R^2$ is H, F, Cl, Br or cyano;

R³ is F, Cl, Br, C₁-C₄ haloalkyl or C₁-C₄ haloalkoxy;
R⁴ᵃ is H, C₁-C₄ alkyl, cyclopropylmethyl or 1-cyclopropylethyl;
R⁴ᵇ is H or CH₃;
R⁵ is H, F, Cl or Br; and
R⁶ is H, F, Cl or Br;

(b) from 0 to about 20% of one or more biologically active agents other than the carboxamide arthropodicides;
(c) from about 20 to about 50% of water;
(d) from about 20 to about 60% of one or more water-immiscible liquid compounds comprising a methylated seed oil of sunflower, soybean, cotton, linseed, or rapeseed; and
(e) from about 3 to about 20% of a surfactant component comprising from about 1 to about 5% of (e1) a surfactant having a dispersing property, from about 2 to about 7% of (e2) a surfactant having an emulsifying property comprising one or more surfactants selected from anionic surfactants and non-ionic surfactants, and (e3) one or more surfactants having a wetting property, wherein (e3) does not exceed about 5% of the composition by weight.

2. The composition of claim 1 wherein component (d) comprises a methylated soybean oil.

3. The composition of claim 1 wherein component (e) comprises one or more anionic surfactants selected from acrylic graft copolymers having an HLB number in the range from about 10 to about 16.

4. The composition of claim 1 wherein component (e) comprises a mixture of one or more anionic surfactants selected from alkylarylsulfonates, and one or more non-ionic surfactants selected from ethoxylated sorbitol esters, ethoxylated sorbitan esters, ethoxylated fatty acid esters, and mixtures thereof.

5. The composition of claim 3 wherein component (e) comprises one or more anionic surfactants selected from alkylbenzenesulfonates.

6. The composition of claim 3 wherein component (e) comprises one or more non-ionic surfactants selected from ethoxylated sorbitol esters and ethoxylated sorbitan esters.

7. The composition of claim 3 wherein component (e) comprises one or more ethoxylated vegetable oils.

8. The composition of claim 1 wherein component (b) is selected from abamectin, acetamiprid, amitraz, avermectin, azadirachtin, bifenthrin, buprofezin, cartap, chlorfenapyr, chlorpyrifos, clothianidin, cyfluthrin, beta-cyfluthrin, cyhalothrin, lambda-cyhalothrin, cypermethrin, cyromazine, deltamethrin, dieldrin, dinotefuran, diofenolan, emamectin, endosulfan, esfenvalerate, ethiprole, fenothiocarb, fenoxycarb, fenvalerate, fipronil, flonicamid, flufenoxuron, hexaflumuron, hydramethylnon, imidacloprid, indoxacarb, lufenuron, metaflumizone, methomyl, methoprene, methoxyfenozide, nitenpyram, nithiazine, novaluron, oxamyl, pymetrozine, pyrethrin, pyridaben, pyridalyl, pyriproxyfen, ryanodine, spinetoram, spinosad, spirodiclofen, spiromesifen, tebufenozide, thiacloprid, thiamethoxam, thiodicarb, thiosultap-sodium, tralomethrin, triazamate, triflumuron, *Bacillus thuringiensis* subsp. *aizawai*, *Bacillus thuringiensis* subsp. *kurstaki*, nucleopolyhedro virus and an encapsulated delta-endotoxin of *Bacillus thuringiensis*.

9. The composition of claim 1 wherein component (e) comprises one or more non-ionic surfactants selected from polyoxyethylene alkyl ethers and polyoxyethylene/polyoxypropylene copolymers.

10. The composition of claim 1 wherein component (a) is 3-bromo-1-(3-chloro-2-pyridinyl)-N-[4-cyano-2-methyl-6-[(methylamino)carbonyl]phenyl]-1H-pyrazole-5-carboxamide.

11. The composition of claim 1 wherein component (a) is 3-bromo-N-[4-chloro-2-methyl-6-[(methylamino)carbonyl]phenyl]-1-(3-chloro-2-pyridinyl)-1H-pyrazole-5-carboxamide.

12. The composition of claim 1 wherein component (c) is an aqueous phase and wherein the one or more carboxamide arthropodicides of component (a) are present as solid particles and at least 90% of the solid particles are suspended or dispersed in the aqueous phase.

13. The composition of claim 12 wherein component (d) is dispersed in the aqueous phase in the form of droplets.

14. A method for controlling the arthropod pest, comprising diluting an arthropodicidal suspension concentrate composition of claim 1 with water, optionally adding an adjuvant, to form a diluted composition, and contacting the arthropod pest or its environment with an effective amount of said diluted composition.

* * * * *